(12) United States Patent
Cramer

(10) Patent No.: US 12,090,020 B2
(45) Date of Patent: Sep. 17, 2024

(54) APPARATUSES AND METHODS ASSISTING IN DENTAL THERAPIES

(71) Applicant: ALIGN TECHNOLOGY, INC., San Jose, CA (US)

(72) Inventor: Christopher Eric Cramer, Durham, NC (US)

(73) Assignee: Align Technology, Inc., San Jose, CA (US)

( * ) Notice: Subject to any disclaimer, the term of this patent is extended or adjusted under 35 U.S.C. 154(b) by 1638 days.

(21) Appl. No.: 15/937,569

(22) Filed: Mar. 27, 2018

(65) Prior Publication Data

US 2018/0280118 A1   Oct. 4, 2018

Related U.S. Application Data

(60) Provisional application No. 62/477,389, filed on Mar. 27, 2017.

(51) Int. Cl.
| | | |
|---|---|---|
| *G16H 10/60* | (2018.01) | |
| *A61C 7/00* | (2006.01) | |
| *A61C 19/04* | (2006.01) | |
| *G16H 20/30* | (2018.01) | |
| *G16H 20/40* | (2018.01) | |

(Continued)

(52) U.S. Cl.
CPC ............. *A61C 7/002* (2013.01); *A61C 19/04* (2013.01); *G16H 10/60* (2018.01); *G16H 20/30* (2018.01); *G16H 20/40* (2018.01); *G16H 50/20* (2018.01); *A61C 2007/004* (2013.01); *A61C 7/08* (2013.01); *B33Y 50/00* (2014.12); *B33Y 80/00* (2014.12); *G16H 50/50* (2018.01)

(58) Field of Classification Search
CPC ........ G16H 20/40; G16H 50/50; G16H 10/60; G16H 50/20; G16H 50/70
See application file for complete search history.

(56) References Cited

U.S. PATENT DOCUMENTS

| 2,171,695 A | 9/1939 | Harper |
| 2,194,790 A | 3/1940 | Gluck |

(Continued)

FOREIGN PATENT DOCUMENTS

| AU | 517102 B | 11/1977 |
| AU | 3031677 A | 11/1977 |

(Continued)

OTHER PUBLICATIONS

US 8,553,966 B1, 10/2013, Alpern et al. (withdrawn)

(Continued)

*Primary Examiner* — Mark Holcomb
(74) *Attorney, Agent, or Firm* — Shay Glenn LLP

(57) ABSTRACT

Provided herein are methods and apparatuses for recommending tooth leveling (e.g., one or more of anterior leveling, posterior leveling, and arch-shape recommendations) for orthodontic devices and methods for patients. Factors involved in the leveling of teeth can include symmetry, doctor preferences, preferences regarding gender, the country in which the patient is being treated, and other issues related to the aesthetics of the mouth and arch shape. The device can comprise an aligner configured to fit over a patient's teeth. Methods of designing and manufacturing aligners based on leveling recommendations are also provided.

13 Claims, 12 Drawing Sheets

(51) Int. Cl.
*G16H 50/20* (2018.01)
*A61C 7/08* (2006.01)
*B33Y 50/00* (2015.01)
*B33Y 80/00* (2015.01)
*G16H 50/50* (2018.01)

(56) References Cited

U.S. PATENT DOCUMENTS

| | | |
|---|---|---|
| 2,467,432 A | 4/1949 | Kesling |
| 2,531,222 A | 11/1950 | Kesling |
| 3,089,487 A | 5/1963 | Enicks et al. |
| 3,092,907 A | 6/1963 | Traiger |
| 3,178,820 A | 4/1965 | Kesling |
| 3,211,143 A | 10/1965 | Grossberg |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,724,075 A | 4/1973 | Kesling |
| 3,738,005 A | 6/1973 | Cohen et al. |
| 3,797,115 A | 3/1974 | Silverman et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,955,282 A | 5/1976 | McNall |
| 3,983,628 A | 10/1976 | Acevedo |
| 4,014,096 A | 3/1977 | Dellinger |
| 4,055,895 A | 11/1977 | Huge |
| 4,094,068 A | 6/1978 | Schinhammer |
| 4,117,596 A | 10/1978 | Wallshein |
| 4,129,946 A | 12/1978 | Kennedy |
| 4,134,208 A | 1/1979 | Pearlman |
| 4,139,944 A | 2/1979 | Bergersen |
| 4,179,811 A | 12/1979 | Hinz |
| 4,179,812 A | 12/1979 | White |
| 4,183,141 A | 1/1980 | Dellinger |
| 4,195,046 A | 3/1980 | Kesling |
| 4,204,325 A | 5/1980 | Kaelble |
| 4,253,828 A | 3/1981 | Coles et al. |
| 4,255,138 A | 3/1981 | Frohn |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,368,040 A | 1/1983 | Weissman |
| 4,419,992 A | 12/1983 | Chorbajian |
| 4,433,956 A | 2/1984 | Witzig |
| 4,433,960 A | 2/1984 | Garito et al. |
| 4,439,154 A | 3/1984 | Mayclin |
| 4,449,928 A | 5/1984 | von Weissenfluh |
| 4,478,580 A | 10/1984 | Barrut |
| 4,500,294 A | 2/1985 | Lewis |
| 4,505,672 A | 3/1985 | Kurz |
| 4,505,673 A | 3/1985 | Yoshii |
| 4,519,386 A | 5/1985 | Sullivan |
| 4,523,908 A | 6/1985 | Drisaldi et al. |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A | 12/1986 | Lauks et al. |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,830,612 A | 5/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,932,866 A | 6/1990 | Guis |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,971,557 A | 11/1990 | Martin |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,015,183 A | 5/1991 | Fenick |
| 5,017,133 A | 5/1991 | Miura |
| 5,018,969 A | 5/1991 | Andreiko et al. |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,061,839 A | 10/1991 | Matsuno et al. |
| 5,083,919 A | 1/1992 | Quach |
| 5,094,614 A | 3/1992 | Wildman |
| 5,100,316 A | 3/1992 | Wildman |
| 5,103,838 A | 4/1992 | Yousif |
| 5,114,339 A | 5/1992 | Guis |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,194,003 A | 3/1993 | Garay et al. |
| 5,204,670 A | 4/1993 | Stinton |
| 5,222,499 A | 6/1993 | Allen et al. |
| 5,224,049 A | 6/1993 | Mushabac |
| 5,238,404 A | 8/1993 | Andreiko |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,314,335 A | 5/1994 | Fung |
| 5,324,186 A | 6/1994 | Bakanowski |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,344,315 A | 9/1994 | Hanson |
| 5,368,478 A | 11/1994 | Andreiko et al. |
| 5,372,502 A | 12/1994 | Massen et al. |
| D354,355 S | 1/1995 | Hilgers |

(56) References Cited

U.S. PATENT DOCUMENTS

| | | |
|---|---|---|
| 5,382,164 A | 1/1995 | Stern |
| 5,395,238 A | 3/1995 | Andreiko et al. |
| 5,415,542 A | 5/1995 | Kesling |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,449,703 A | 9/1995 | Mitra et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,487,662 A | 1/1996 | Kipke et al. |
| RE35,169 E | 3/1996 | Lemchen et al. |
| 5,499,633 A | 3/1996 | Fenton |
| 5,522,725 A | 6/1996 | Jordan et al. |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,575,655 A | 11/1996 | Darnell |
| 5,583,977 A | 12/1996 | Seidl |
| 5,587,912 A | 12/1996 | Andersson et al. |
| 5,588,098 A | 12/1996 | Chen et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,636,736 A | 6/1997 | Jacobs et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,711,665 A | 1/1998 | Adam et al. |
| 5,711,666 A | 1/1998 | Hanson |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,162 A | 9/1998 | Shimodaira et al. |
| 5,800,174 A | 9/1998 | Andersson |
| 5,813,854 A | 9/1998 | Nikodem |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,876,199 A | 3/1999 | Bergersen |
| 5,879,158 A | 3/1999 | Doyle et al. |
| 5,880,961 A | 3/1999 | Crump |
| 5,880,962 A | 3/1999 | Andersson et al. |
| 5,882,192 A | 3/1999 | Bergersen |
| 5,886,702 A | 3/1999 | Migdal et al. |
| 5,890,896 A | 4/1999 | Padial |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,975,906 A | 11/1999 | Knutson |
| 5,980,246 A | 11/1999 | Ramsay et al. |
| 5,989,023 A | 11/1999 | Summer et al. |
| 6,002,706 A | 12/1999 | Staver et al. |
| 6,018,713 A | 1/2000 | Coli et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,070,140 A | 5/2000 | Tran |
| 6,099,303 A | 8/2000 | Gibbs et al. |
| 6,099,314 A | 8/2000 | Kopelman et al. |
| 6,102,701 A | 8/2000 | Engeron |
| 6,120,287 A | 9/2000 | Chen |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,183,249 B1 | 2/2001 | Brennan et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,210,162 B1 | 4/2001 | Chishti et al. |
| 6,212,435 B1 | 4/2001 | Lattner et al. |
| 6,213,767 B1 | 4/2001 | Dixon et al. |
| 6,217,334 B1 | 4/2001 | Hultgren |
| 6,227,850 B1 | 5/2001 | Chishti et al. |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,283,761 B1 | 9/2001 | Joao |
| 6,288,138 B1 | 9/2001 | Yamamoto |
| 6,299,438 B1 | 10/2001 | Sahagian et al. |
| 6,309,215 B1 | 10/2001 | Phan et al. |
| 6,313,432 B1 | 11/2001 | Nagata et al. |
| 6,315,553 B1 | 11/2001 | Sachdeva et al. |
| 6,328,745 B1 | 12/2001 | Ascherman |
| 6,332,774 B1 | 12/2001 | Chikami |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,386,878 B1 | 5/2002 | Pavlovskaia et al. |
| 6,394,802 B1 | 5/2002 | Hahn |
| 6,402,510 B1 | 6/2002 | Williams |
| 6,402,707 B1 | 6/2002 | Ernst |
| 6,405,729 B1 | 6/2002 | Thornton |
| 6,406,292 B1 | 6/2002 | Chishti et al. |
| 6,409,504 B1 | 6/2002 | Jones et al. |
| 6,413,086 B1 | 7/2002 | Womack |
| 6,414,264 B1 | 7/2002 | von Falkenhausen |
| 6,414,708 B1 | 7/2002 | Carmeli et al. |
| 6,435,871 B1 | 8/2002 | Inman |
| 6,436,058 B1 | 8/2002 | Krahner et al. |
| 6,441,354 B1 | 8/2002 | Seghatol et al. |
| 6,450,167 B1 | 9/2002 | David et al. |
| 6,450,807 B1 | 9/2002 | Chishti et al. |
| 6,462,301 B1 | 10/2002 | Scott et al. |
| 6,470,338 B1 | 10/2002 | Rizzo et al. |
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,009 B1 | 2/2003 | Wilkins |

(56) References Cited

U.S. PATENT DOCUMENTS

| | | |
|---|---|---|
| 6,523,019 B1 | 2/2003 | Borthwick |
| 6,524,101 B1 | 2/2003 | Phan et al. |
| 6,526,168 B1 | 2/2003 | Ornes et al. |
| 6,526,982 B1 | 3/2003 | Strong |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Amuah |
| 6,542,881 B1 | 4/2003 | Meidan et al. |
| 6,542,894 B1 | 4/2003 | Lee et al. |
| 6,542,903 B2 | 4/2003 | Hull et al. |
| 6,551,243 B2 | 4/2003 | Bocionek et al. |
| 6,554,837 B1 | 4/2003 | Hauri et al. |
| 6,556,659 B1 | 4/2003 | Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |
| 6,573,998 B2 | 6/2003 | Sabban |
| 6,574,561 B2 | 6/2003 | Alexander et al. |
| 6,578,003 B1 | 6/2003 | Camarda et al. |
| 6,580,948 B2 | 6/2003 | Haupert et al. |
| 6,587,529 B1 | 7/2003 | Staszewski et al. |
| 6,587,828 B1 | 7/2003 | Sachdeva |
| 6,592,368 B1 | 7/2003 | Weathers |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B2 | 7/2003 | Webb et al. |
| 6,602,070 B2 | 8/2003 | Miller et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinbold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,682,346 B2 | 1/2004 | Chishti et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,736,638 B1 | 5/2004 | Sachdeva et al. |
| 6,739,869 B2 | 5/2004 | Taub et al. |
| 6,744,932 B1 | 6/2004 | Rubbert et al. |
| 6,749,414 B1 | 6/2004 | Hanson et al. |
| 6,769,913 B2 | 8/2004 | Hurson |
| 6,772,026 B2 | 8/2004 | Bradbury et al. |
| 6,790,036 B2 | 9/2004 | Graham |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,832,912 B2 | 12/2004 | Mao |
| 6,832,914 B1 | 12/2004 | Bonnet et al. |
| 6,843,370 B2 | 1/2005 | Tuneberg |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,976,841 B1 | 12/2005 | Osterwalder |
| 6,978,268 B2 | 12/2005 | Thomas et al. |
| 6,983,752 B2 | 1/2006 | Garabadian |
| 6,984,128 B2 | 1/2006 | Breining et al. |
| 6,988,893 B2 | 1/2006 | Haywood |
| 7,016,952 B2 | 3/2006 | Mullen et al. |
| 7,020,963 B2 | 4/2006 | Cleary et al. |
| 7,036,514 B2 | 5/2006 | Heck |
| 7,040,896 B2 | 5/2006 | Pavlovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 | 1/2007 | Choi et al. |
| 7,166,063 B2 | 1/2007 | Rahman et al. |
| 7,184,150 B2 | 2/2007 | Quadling et al. |
| 7,191,451 B2 | 3/2007 | Nakagawa |
| 7,192,273 B2 | 3/2007 | McSurdy |
| 7,217,131 B2 | 5/2007 | Vuillemot |
| 7,220,122 B2 | 5/2007 | Chishti |
| 7,220,124 B2 | 5/2007 | Taub et al. |
| 7,229,282 B2 | 6/2007 | Andreiko et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,245,753 B2 | 7/2007 | Squilla et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,294,141 B2 | 11/2007 | Bergersen |
| 7,302,842 B2 | 12/2007 | Biester et al. |
| 7,320,592 B2 | 1/2008 | Chishti et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,354,270 B2 | 4/2008 | Abolfathi et al. |
| 7,357,637 B2 | 4/2008 | Liechtung |
| 7,435,083 B2 | 10/2008 | Chishti et al. |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,543,511 B2 | 6/2009 | Kimura et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |

(56) References Cited

U.S. PATENT DOCUMENTS

| | | | |
|---|---|---|---|
| 7,632,216 B2 | 12/2009 | Rahman et al. |
| 7,633,625 B1 | 12/2009 | Woollam et al. |
| 7,637,262 B2 | 12/2009 | Bailey |
| 7,637,740 B2 | 12/2009 | Knopp |
| 7,641,473 B2 | 1/2010 | Sporbert et al. |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |
| 7,728,848 B2 | 6/2010 | Petrov et al. |
| 7,731,508 B2 | 6/2010 | Borst |
| 7,735,217 B2 | 6/2010 | Borst |
| 7,740,476 B2 | 6/2010 | Rubbert et al. |
| 7,744,369 B2 | 6/2010 | Imgrund et al. |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,841,464 B2 | 11/2010 | Cinader et al. |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,869,983 B2 | 1/2011 | Raby et al. |
| 7,872,760 B2 | 1/2011 | Ertl |
| 7,874,836 B2 | 1/2011 | McSurdy |
| 7,874,837 B2 | 1/2011 | Chishti et al. |
| 7,874,849 B2 | 1/2011 | Sticker et al. |
| 7,878,801 B2 | 2/2011 | Abolfathi et al. |
| 7,878,805 B2 | 2/2011 | Moss et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,970,627 B2 | 6/2011 | Kuo et al. |
| 7,985,414 B2 | 7/2011 | Knaack et al. |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,029,277 B2 | 10/2011 | Imgrund et al. |
| 8,038,444 B2 | 10/2011 | Kitching et al. |
| 8,045,772 B2 | 10/2011 | Kosuge et al. |
| 8,054,556 B2 | 11/2011 | Chen et al. |
| 8,070,490 B1 | 12/2011 | Roetzer et al. |
| 8,075,306 B2 | 12/2011 | Kitching et al. |
| 8,077,949 B2 | 12/2011 | Liang et al. |
| 8,083,556 B2 | 12/2011 | Stadler et al. |
| D652,799 S | 1/2012 | Mueller |
| 8,092,215 B2 | 1/2012 | Stone-Collonge et al. |
| 8,095,383 B2 | 1/2012 | Arnone et al. |
| 8,099,268 B2 | 1/2012 | Kitching et al. |
| 8,099,305 B2 | 1/2012 | Kuo et al. |
| 8,118,592 B2 | 2/2012 | Tortorici |
| 8,126,025 B2 | 2/2012 | Takeda |
| 8,136,529 B2 | 3/2012 | Kelly |
| 8,144,954 B2 | 3/2012 | Quadling et al. |
| 8,160,334 B2 | 4/2012 | Thiel et al. |
| 8,172,569 B2 | 5/2012 | Matty et al. |
| 8,197,252 B1 | 6/2012 | Harrison |
| 8,201,560 B2 | 6/2012 | Dembro |
| 8,215,312 B2 | 7/2012 | Garabadian et al. |
| 8,240,018 B2 | 8/2012 | Walter et al. |
| 8,275,180 B2 | 9/2012 | Kuo |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,401,826 B2 | 3/2013 | Cheng et al. |
| 8,419,428 B2 | 4/2013 | Lawrence |
| 8,433,083 B2 | 4/2013 | Abolfathi et al. |
| 8,439,672 B2 | 5/2013 | Matov et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,517,726 B2 | 8/2013 | Kakavand et al. |
| 8,520,922 B2 | 8/2013 | Wang et al. |
| 8,520,925 B2 | 8/2013 | Duret et al. |
| 8,523,565 B2 | 9/2013 | Matty et al. |
| 8,545,221 B2 | 10/2013 | Stone-Collonge et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,583,586 B2 * | 11/2013 | Ebadollahi ............ G06N 20/00 706/53 |
| 8,601,925 B1 | 12/2013 | Coto |
| 8,639,477 B2 | 1/2014 | Chelnokov et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,738,394 B2 | 5/2014 | Kuo |
| 8,743,923 B2 | 6/2014 | Geske et al. |
| 8,753,114 B2 | 6/2014 | Vuillemot |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,843,381 B2 | 9/2014 | Kuo et al. |
| 8,856,053 B2 | 10/2014 | Mah |
| 8,870,566 B2 | 10/2014 | Bergersen |
| 8,874,452 B2 | 10/2014 | Kuo |
| 8,878,905 B2 | 11/2014 | Fisker et al. |
| 8,899,976 B2 | 12/2014 | Chen et al. |
| 8,936,463 B2 | 1/2015 | Mason et al. |
| 8,944,812 B2 | 2/2015 | Kuo |
| 8,948,482 B2 | 2/2015 | Levin |
| 8,956,058 B2 | 2/2015 | Rösch |
| 8,992,216 B2 | 3/2015 | Karazivan |
| 9,004,915 B2 | 4/2015 | Moss et al. |
| 9,022,792 B2 | 5/2015 | Sticker et al. |
| 9,039,418 B1 | 5/2015 | Rubbert |
| 9,084,535 B2 | 7/2015 | Girkin et al. |
| 9,084,657 B2 | 7/2015 | Matty et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,211,166 B2 | 12/2015 | Kuo et al. |
| 9,214,014 B2 | 12/2015 | Levin |
| 9,220,580 B2 | 12/2015 | Borovinskih et al. |
| 9,241,774 B2 | 1/2016 | Li et al. |
| 9,242,118 B2 | 1/2016 | Brawn |
| 9,261,358 B2 | 2/2016 | Atiya et al. |
| 9,277,972 B2 | 3/2016 | Brandt et al. |
| 9,336,336 B2 | 5/2016 | Deichmann et al. |
| 9,351,810 B2 | 5/2016 | Moon |
| 9,375,300 B2 | 6/2016 | Matov et al. |
| 9,403,238 B2 | 8/2016 | Culp |
| 9,408,743 B1 | 8/2016 | Wagner |
| 9,414,897 B2 | 8/2016 | Wu et al. |
| 9,433,476 B2 | 9/2016 | Khardekar et al. |
| 9,439,568 B2 | 9/2016 | Atiya et al. |

(56) References Cited

U.S. PATENT DOCUMENTS

| | | |
|---|---|---|
| 9,444,981 B2 | 9/2016 | Bellis et al. |
| 9,463,287 B1 | 10/2016 | Lorberbaum et al. |
| 9,492,243 B2 | 11/2016 | Kuo |
| 9,500,635 B2 | 11/2016 | Islam |
| 9,506,808 B2 | 11/2016 | Jeon et al. |
| 9,510,918 B2 | 12/2016 | Sanchez |
| 9,545,331 B2 | 1/2017 | Ingemarsson-Matzen |
| 9,566,132 B2 | 2/2017 | Stone-Collonge et al. |
| 9,584,771 B2 | 2/2017 | Mandelis et al. |
| 9,589,329 B2 | 3/2017 | Levin |
| 9,675,427 B2 | 6/2017 | Kopelman |
| 9,675,430 B2 | 6/2017 | Verker et al. |
| 9,693,839 B2 | 7/2017 | Atiya et al. |
| 9,744,006 B2 | 8/2017 | Ross |
| 9,820,829 B2 | 11/2017 | Kuo |
| 9,830,688 B2 | 11/2017 | Levin |
| 9,844,421 B2 | 12/2017 | Moss et al. |
| 9,848,985 B2 | 12/2017 | Yang et al. |
| 9,861,451 B1 | 1/2018 | Davis |
| 9,936,186 B2 | 4/2018 | Jesenko et al. |
| 10,123,853 B2 | 11/2018 | Moss et al. |
| 10,159,541 B2 | 12/2018 | Bindayel |
| 10,172,693 B2 | 1/2019 | Brandt et al. |
| 10,195,690 B2 | 2/2019 | Culp |
| 10,231,801 B2 | 3/2019 | Korytov et al. |
| 10,238,472 B2 | 3/2019 | Levin |
| 10,258,432 B2 | 4/2019 | Webber |
| 11,096,763 B2 * | 8/2021 | Akopov .......... A61C 7/002 |
| 2001/0002310 A1 | 5/2001 | Chishti et al. |
| 2001/0032100 A1 | 10/2001 | Mahmud et al. |
| 2001/0038705 A1 | 11/2001 | Rubbert et al. |
| 2001/0041320 A1 | 11/2001 | Phan et al. |
| 2002/0004727 A1 | 1/2002 | Knaus et al. |
| 2002/0007284 A1 | 1/2002 | Schurenberg et al. |
| 2002/0010568 A1 | 1/2002 | Rubbert et al. |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0035572 A1 | 3/2002 | Takatori et al. |
| 2002/0064752 A1 | 5/2002 | Durbin et al. |
| 2002/0064759 A1 | 5/2002 | Durbin et al. |
| 2002/0087551 A1 | 7/2002 | Hickey et al. |
| 2002/0107853 A1 | 8/2002 | Hofmann et al. |
| 2002/0188478 A1 | 12/2002 | Breeland et al. |
| 2002/0192617 A1 | 12/2002 | Phan et al. |
| 2003/0000927 A1 | 1/2003 | Kanaya et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0059736 A1 | 3/2003 | Lai et al. |
| 2003/0060532 A1 | 3/2003 | Subelka et al. |
| 2003/0068598 A1 | 4/2003 | Vallittu et al. |
| 2003/0095697 A1 | 5/2003 | Wood et al. |
| 2003/0101079 A1 | 5/2003 | McLaughlin |
| 2003/0103060 A1 | 6/2003 | Anderson et al. |
| 2003/0120517 A1 | 6/2003 | Eida et al. |
| 2003/0139834 A1 | 7/2003 | Nikolskiy et al. |
| 2003/0144886 A1 | 7/2003 | Taira |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0215764 A1 | 11/2003 | Kopelman et al. |
| 2003/0224311 A1 | 12/2003 | Cronauer |
| 2003/0224313 A1 | 12/2003 | Bergersen |
| 2003/0224314 A1 | 12/2003 | Bergersen |
| 2004/0002873 A1 | 1/2004 | Sachdeva |
| 2004/0009449 A1 | 1/2004 | Mah et al. |
| 2004/0013994 A1 | 1/2004 | Goldberg et al. |
| 2004/0019262 A1 | 1/2004 | Perelgut |
| 2004/0029078 A1 | 2/2004 | Marshall |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0080621 A1 | 4/2004 | Fisher et al. |
| 2004/0094165 A1 | 5/2004 | Cook |
| 2004/0107118 A1 | 6/2004 | Harnsberger et al. |
| 2004/0133083 A1 | 7/2004 | Comaniciu et al. |
| 2004/0152036 A1 | 8/2004 | Abolfathi |
| 2004/0158194 A1 | 8/2004 | Wolff et al. |
| 2004/0166463 A1 | 8/2004 | Wen et al. |
| 2004/0167646 A1 | 8/2004 | Jelonek et al. |
| 2004/0170941 A1 | 9/2004 | Phan et al. |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0219479 A1 | 11/2004 | Malin et al. |
| 2004/0220691 A1 | 11/2004 | Hofmeister et al. |
| 2004/0229185 A1 | 11/2004 | Knopp |
| 2004/0259049 A1 | 12/2004 | Kopelman et al. |
| 2005/0003318 A1 | 1/2005 | Choi et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |
| 2005/0040551 A1 | 2/2005 | Biegler et al. |
| 2005/0042569 A1 | 2/2005 | Plan et al. |
| 2005/0042577 A1 | 2/2005 | Kvitrud et al. |
| 2005/0048433 A1 | 3/2005 | Hilliard |
| 2005/0074717 A1 | 4/2005 | Cleary et al. |
| 2005/0089822 A1 | 4/2005 | Geng |
| 2005/0100333 A1 | 5/2005 | Kerschbaumer et al. |
| 2005/0108052 A1 | 5/2005 | Omaboe |
| 2005/0131738 A1 | 6/2005 | Morris |
| 2005/0144150 A1 | 6/2005 | Ramamurthy et al. |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0216314 A1 | 9/2005 | Secor |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0244791 A1 | 11/2005 | Davis et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0093982 A1 | 5/2006 | Wen |
| 2006/0098007 A1 | 5/2006 | Rouet et al. |
| 2006/0099545 A1 | 5/2006 | Lia et al. |
| 2006/0099546 A1 | 5/2006 | Bergersen |
| 2006/0110698 A1 | 5/2006 | Robson |
| 2006/0111631 A1 | 5/2006 | Kelliher et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0154207 A1 | 7/2006 | Kuo |
| 2006/0173715 A1 | 8/2006 | Wang |
| 2006/0183082 A1 | 8/2006 | Quadling et al. |
| 2006/0188834 A1 | 8/2006 | Hilliard |
| 2006/0188848 A1 | 8/2006 | Tricca et al. |
| 2006/0194163 A1 | 8/2006 | Tricca et al. |
| 2006/0199153 A1 | 9/2006 | Liu et al. |
| 2006/0204078 A1 | 9/2006 | Orth et al. |
| 2006/0223022 A1 | 10/2006 | Solomon |
| 2006/0223023 A1 | 10/2006 | Lai et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fornoff |
| 2006/0275731 A1 | 12/2006 | Wen et al. |

(56) References Cited

U.S. PATENT DOCUMENTS

| | | |
|---|---|---|
| 2006/0275736 A1 | 12/2006 | Wen et al. |
| 2006/0277075 A1 | 12/2006 | Salwan |
| 2006/0290693 A1 | 12/2006 | Zhou et al. |
| 2006/0292520 A1 | 12/2006 | Dillon et al. |
| 2007/0031775 A1 | 2/2007 | Andreiko |
| 2007/0046865 A1 | 3/2007 | Umeda et al. |
| 2007/0053048 A1 | 3/2007 | Kumar et al. |
| 2007/0054237 A1 | 3/2007 | Neuschafer |
| 2007/0065768 A1 | 3/2007 | Nadav |
| 2007/0087300 A1 | 4/2007 | Willison et al. |
| 2007/0087302 A1 | 4/2007 | Reising et al. |
| 2007/0106138 A1 | 5/2007 | Beiski et al. |
| 2007/0122592 A1 | 5/2007 | Anderson et al. |
| 2007/0128574 A1 | 6/2007 | Kuo et al. |
| 2007/0141525 A1 | 6/2007 | Cinader, Jr. |
| 2007/0141526 A1 | 6/2007 | Eisenberg et al. |
| 2007/0143135 A1 | 6/2007 | Lindquist et al. |
| 2007/0168152 A1 | 7/2007 | Matov et al. |
| 2007/0172112 A1 | 7/2007 | Paley et al. |
| 2007/0172291 A1 | 7/2007 | Yokoyama |
| 2007/0178420 A1 | 8/2007 | Keski-Nisula et al. |
| 2007/0183633 A1 | 8/2007 | Hoffmann |
| 2007/0184402 A1 | 8/2007 | Boutoussov et al. |
| 2007/0185732 A1 | 8/2007 | Hicks et al. |
| 2007/0192137 A1 | 8/2007 | Ombrellaro |
| 2007/0199929 A1 | 8/2007 | Rippl et al. |
| 2007/0215582 A1 | 9/2007 | Roeper et al. |
| 2007/0218422 A1 | 9/2007 | Ehrenfeld |
| 2007/0231765 A1 | 10/2007 | Phan et al. |
| 2007/0238065 A1* | 10/2007 | Sherwood ............... A61C 7/08 433/24 |
| 2007/0239488 A1 | 10/2007 | DeRosso |
| 2007/0263226 A1 | 11/2007 | Kurtz et al. |
| 2008/0013727 A1 | 1/2008 | Uemura |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057467 A1 | 3/2008 | Gittelson |
| 2008/0057479 A1 | 3/2008 | Grenness |
| 2008/0059238 A1 | 3/2008 | Park et al. |
| 2008/0090208 A1 | 4/2008 | Rubbert |
| 2008/0094389 A1 | 4/2008 | Rouet et al. |
| 2008/0113317 A1 | 5/2008 | Kemp et al. |
| 2008/0115791 A1 | 5/2008 | Heine |
| 2008/0118882 A1 | 5/2008 | Su |
| 2008/0118886 A1 | 5/2008 | Liang et al. |
| 2008/0141534 A1 | 6/2008 | Hilliard |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0248443 A1 | 10/2008 | Chishti et al. |
| 2008/0254403 A1 | 10/2008 | Hilliard |
| 2008/0268400 A1 | 10/2008 | Moss et al. |
| 2008/0306724 A1 | 12/2008 | Kitching et al. |
| 2009/0029310 A1 | 1/2009 | Pumphrey et al. |
| 2009/0030290 A1 | 1/2009 | Kozuch et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0087050 A1 | 4/2009 | Gandyra |
| 2009/0098502 A1 | 4/2009 | Andreiko |
| 2009/0099445 A1 | 4/2009 | Burger |
| 2009/0103579 A1 | 4/2009 | Ushimaru et al. |
| 2009/0105523 A1 | 4/2009 | Kassayan et al. |
| 2009/0130620 A1 | 5/2009 | Yazdi et al. |
| 2009/0136890 A1 | 5/2009 | Kang et al. |
| 2009/0136893 A1 | 5/2009 | Zegarelli |
| 2009/0148809 A1 | 6/2009 | Kuo et al. |
| 2009/0170050 A1 | 7/2009 | Marcus |
| 2009/0181346 A1 | 7/2009 | Orth |
| 2009/0191502 A1 | 7/2009 | Cao et al. |
| 2009/0210032 A1 | 8/2009 | Beiski et al. |
| 2009/0218514 A1 | 9/2009 | Klunder et al. |
| 2009/0246726 A1 | 10/2009 | Chelnokov et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0316966 A1 | 12/2009 | Marshall et al. |
| 2009/0317757 A1 | 12/2009 | Lemchen |
| 2010/0015565 A1 | 1/2010 | Carrillo Gonzalez et al. |
| 2010/0019170 A1 | 1/2010 | Hart et al. |
| 2010/0028825 A1 | 2/2010 | Lemchen |
| 2010/0045902 A1 | 2/2010 | Ikeda et al. |
| 2010/0062394 A1 | 3/2010 | Jones et al. |
| 2010/0068676 A1 | 3/2010 | Mason et al. |
| 2010/0086890 A1 | 4/2010 | Kuo |
| 2010/0106518 A1* | 4/2010 | Kuo ....................... G06Q 10/10 705/2 |
| 2010/0138025 A1 | 6/2010 | Morton et al. |
| 2010/0142789 A1 | 6/2010 | Chang et al. |
| 2010/0145664 A1 | 6/2010 | Hultgren et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0179789 A1 | 7/2010 | Sachdeva et al. |
| 2010/0193482 A1 | 8/2010 | Ow et al. |
| 2010/0196837 A1 | 8/2010 | Farrell |
| 2010/0216085 A1 | 8/2010 | Kopelman |
| 2010/0217130 A1 | 8/2010 | Weinlaender |
| 2010/0231577 A1 | 9/2010 | Kim et al. |
| 2010/0268363 A1 | 10/2010 | Karim et al. |
| 2010/0268515 A1 | 10/2010 | Vogt et al. |
| 2010/0279243 A1 | 11/2010 | Cinader et al. |
| 2010/0280798 A1 | 11/2010 | Pattijn |
| 2010/0281370 A1 | 11/2010 | Rohaly et al. |
| 2010/0303316 A1 | 12/2010 | Bullis et al. |
| 2010/0312484 A1 | 12/2010 | DuHamel et al. |
| 2010/0327461 A1 | 12/2010 | Co et al. |
| 2011/0007920 A1 | 1/2011 | Abolfathi et al. |
| 2011/0012901 A1 | 1/2011 | Kaplanyan |
| 2011/0045428 A1 | 2/2011 | Boltunov et al. |
| 2011/0056350 A1 | 3/2011 | Gale et al. |
| 2011/0081625 A1 | 4/2011 | Fuh |
| 2011/0091832 A1 | 4/2011 | Kim et al. |
| 2011/0102549 A1 | 5/2011 | Takahashi |
| 2011/0102566 A1 | 5/2011 | Zakian et al. |
| 2011/0104630 A1 | 5/2011 | Matov et al. |
| 2011/0136072 A1 | 6/2011 | Li et al. |
| 2011/0136090 A1 | 6/2011 | Kazemi |
| 2011/0143300 A1 | 6/2011 | Villalba |
| 2011/0143673 A1 | 6/2011 | Landesman et al. |
| 2011/0159452 A1 | 6/2011 | Huang |
| 2011/0164810 A1 | 7/2011 | Zang et al. |
| 2011/0207072 A1 | 8/2011 | Schiemann |
| 2011/0212420 A1 | 9/2011 | Vuillemot |
| 2011/0220623 A1 | 9/2011 | Beutler |
| 2011/0235045 A1 | 9/2011 | Koerner et al. |
| 2011/0269092 A1 | 11/2011 | Kuo et al. |
| 2011/0282473 A1* | 11/2011 | Pavlovskaia ........... G06V 10/46 700/98 |
| 2011/0316994 A1 | 12/2011 | Lemchen |
| 2012/0028210 A1 | 2/2012 | Hegyi et al. |
| 2012/0029883 A1 | 2/2012 | Heinz et al. |
| 2012/0040311 A1 | 2/2012 | Nilsson |
| 2012/0047105 A1* | 2/2012 | Saigal ..................... G16Z 99/00 706/54 |
| 2012/0064477 A1 | 3/2012 | Schmitt |
| 2012/0081786 A1 | 4/2012 | Mizuyama et al. |
| 2012/0086681 A1 | 4/2012 | Kim et al. |
| 2012/0115107 A1 | 5/2012 | Adams |
| 2012/0129117 A1 | 5/2012 | McCance |
| 2012/0147912 A1 | 6/2012 | Moench et al. |
| 2012/0150494 A1 | 6/2012 | Anderson et al. |
| 2012/0166213 A1 | 6/2012 | Arnone et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0029284 A1 | 1/2013 | Teasdale |

(56) References Cited

U.S. PATENT DOCUMENTS

| | | |
|---|---|---|
| 2013/0081272 A1 | 4/2013 | Johnson et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0163627 A1 | 6/2013 | Seurin et al. |
| 2013/0201488 A1 | 8/2013 | Ishihara |
| 2013/0204599 A1 | 8/2013 | Matov et al. |
| 2013/0209952 A1 | 8/2013 | Kuo et al. |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0278396 A1 | 10/2013 | Kimmel |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2013/0325431 A1 | 12/2013 | See et al. |
| 2013/0337412 A1 | 12/2013 | Kwon |
| 2014/0061974 A1 | 3/2014 | Tyler |
| 2014/0081091 A1 | 3/2014 | Abolfathi et al. |
| 2014/0093160 A1 | 4/2014 | Porikli et al. |
| 2014/0106289 A1 | 4/2014 | Kozlowski |
| 2014/0122027 A1 | 5/2014 | Andreiko et al. |
| 2014/0136222 A1 | 5/2014 | Arnone et al. |
| 2014/0142902 A1 | 5/2014 | Chelnokov et al. |
| 2014/0178829 A1 | 6/2014 | Kim |
| 2014/0265034 A1 | 9/2014 | Dudley |
| 2014/0272774 A1 | 9/2014 | Dillon et al. |
| 2014/0280376 A1 | 9/2014 | Kuo |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0342301 A1 | 11/2014 | Fleer et al. |
| 2014/0350354 A1 | 11/2014 | Stenzler et al. |
| 2014/0363778 A1 | 12/2014 | Parker |
| 2015/0002649 A1 | 1/2015 | Nowak et al. |
| 2015/0004553 A1 | 1/2015 | Li et al. |
| 2015/0021210 A1 | 1/2015 | Kesling |
| 2015/0079531 A1 | 3/2015 | Heine |
| 2015/0094564 A1 | 4/2015 | Tashman et al. |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0132708 A1* | 5/2015 | Kuo ................ A61C 7/08 433/2 |
| 2015/0140502 A1 | 5/2015 | Brawn et al. |
| 2015/0150501 A1 | 6/2015 | George et al. |
| 2015/0164335 A1 | 6/2015 | Van Der Poel et al. |
| 2015/0173856 A1 | 6/2015 | Lowe et al. |
| 2015/0182303 A1 | 7/2015 | Abraham et al. |
| 2015/0216626 A1 | 8/2015 | Ranjbar |
| 2015/0216716 A1 | 8/2015 | Anitua Aldecoa |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0320532 A1 | 11/2015 | Matty et al. |
| 2015/0325044 A1 | 11/2015 | Lebovitz |
| 2015/0338209 A1 | 11/2015 | Knüttel |
| 2015/0351638 A1 | 12/2015 | Amato |
| 2015/0374469 A1 | 12/2015 | Konno et al. |
| 2016/0000332 A1 | 1/2016 | Atiya et al. |
| 2016/0003610 A1 | 1/2016 | Lampert et al. |
| 2016/0042509 A1 | 2/2016 | Andreiko et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0100924 A1 | 4/2016 | Wilson et al. |
| 2016/0106520 A1 | 4/2016 | Borovinskih et al. |
| 2016/0120621 A1 | 5/2016 | Li et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0220105 A1 | 8/2016 | Durent |
| 2016/0220200 A1 | 8/2016 | Sandholm et al. |
| 2016/0225151 A1 | 8/2016 | Cocco et al. |
| 2016/0228213 A1 | 8/2016 | Tod et al. |
| 2016/0242871 A1 | 8/2016 | Morton et al. |
| 2016/0246936 A1 | 8/2016 | Kahn |
| 2016/0287358 A1 | 10/2016 | Nowak et al. |
| 2016/0296303 A1 | 10/2016 | Parker |
| 2016/0302885 A1 | 10/2016 | Matov et al. |
| 2016/0328843 A1 | 11/2016 | Graham et al. |
| 2016/0338799 A1 | 11/2016 | Wu et al. |
| 2016/0346063 A1 | 12/2016 | Schulhof et al. |
| 2016/0367339 A1 | 12/2016 | Khardekar et al. |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0049311 A1 | 2/2017 | Borovinskih et al. |
| 2017/0049326 A1 | 2/2017 | Alfano et al. |
| 2017/0056131 A1 | 3/2017 | Alauddin et al. |
| 2017/0071705 A1 | 3/2017 | Kuo |
| 2017/0086943 A1 | 3/2017 | Mah |
| 2017/0100209 A1 | 4/2017 | Wen |
| 2017/0100212 A1 | 4/2017 | Sherwood et al. |
| 2017/0100213 A1 | 4/2017 | Kuo |
| 2017/0100214 A1 | 4/2017 | Wen |
| 2017/0105815 A1 | 4/2017 | Matov et al. |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0215739 A1 | 8/2017 | Miyasato |
| 2017/0251954 A1 | 9/2017 | Lotan et al. |
| 2017/0258555 A1 | 9/2017 | Kopelman |
| 2017/0265970 A1 | 9/2017 | Verker |
| 2017/0319054 A1 | 11/2017 | Miller et al. |
| 2017/0319296 A1 | 11/2017 | Webber et al. |
| 2017/0325690 A1 | 11/2017 | Salah et al. |
| 2017/0340411 A1 | 11/2017 | Akselrod |
| 2017/0340415 A1 | 11/2017 | Choi et al. |
| 2018/0000563 A1 | 1/2018 | Shanjani et al. |
| 2018/0000565 A1 | 1/2018 | Shanjani et al. |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071054 A1 | 3/2018 | Ha |
| 2018/0071055 A1 | 3/2018 | Kuo |
| 2018/0085059 A1 | 3/2018 | Lee |
| 2018/0096465 A1 | 4/2018 | Levin |
| 2018/0125610 A1 | 5/2018 | Carrier et al. |
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0168788 A1 | 6/2018 | Fernie |
| 2018/0192877 A1 | 7/2018 | Atiya et al. |
| 2018/0228359 A1 | 8/2018 | Meyer et al. |
| 2018/0318043 A1 | 11/2018 | Li et al. |
| 2018/0368944 A1 | 12/2018 | Sato et al. |
| 2019/0026599 A1 | 1/2019 | Salah et al. |
| 2019/0046296 A1 | 2/2019 | Kopelman et al. |
| 2019/0046297 A1 | 2/2019 | Kopelman et al. |
| 2019/0069975 A1 | 3/2019 | Cam et al. |
| 2019/0076216 A1 | 3/2019 | Moss et al. |
| 2019/0090983 A1 | 3/2019 | Webber et al. |

FOREIGN PATENT DOCUMENTS

| | | |
|---|---|---|
| AU | 5598894 A | 6/1994 |
| CA | 1121955 A1 | 4/1982 |
| CN | 1655732 A | 8/2005 |
| CN | 1655733 A | 8/2005 |

(56) References Cited

FOREIGN PATENT DOCUMENTS

| | | |
|---|---|---|
| CN | 102017658 A | 4/2011 |
| CN | 103889364 A | 6/2014 |
| CN | 204092220 U | 1/2015 |
| CN | 105496575 A | 4/2016 |
| CN | 105997274 A | 10/2016 |
| DE | 2749802 A1 | 5/1978 |
| DE | 3526198 A1 | 2/1986 |
| DE | 4207169 A1 | 9/1993 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 202012011899 U1 | 1/2013 |
| DE | 102014225457 A1 | 6/2016 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2867377 A1 | 9/2005 |
| FR | 2930334 A1 | 10/2009 |
| GB | 1550777 A | 8/1979 |
| JP | 53-058191 A | 5/1978 |
| JP | 4028359 A | 1/1992 |
| JP | 08-508174 A | 9/1996 |
| JP | 09-19443 A | 1/1997 |
| JP | 2003245289 A | 9/2003 |
| JP | 2000339468 A | 9/2004 |
| JP | 2005527320 A | 9/2005 |
| JP | 2005527321 A | 9/2005 |
| JP | 2006043121 A | 2/2006 |
| JP | 2007151614 A | 6/2007 |
| JP | 2007260158 A | 10/2007 |
| JP | 2007537824 A | 12/2007 |
| JP | 2008067732 A | 3/2008 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009078133 A | 4/2009 |
| JP | 2009101386 A | 5/2009 |
| JP | 2009205330 A | 9/2009 |
| JP | 2010017726 A | 1/2010 |
| JP | 2011087733 A | 5/2011 |
| JP | 2012045143 A | 3/2012 |
| JP | 2013007645 A | 1/2013 |
| JP | 2013192865 A | 9/2013 |
| JP | 201735173 A | 2/2017 |
| KR | 10-20020062793 A | 7/2002 |
| KR | 10-20070108019 A | 11/2007 |
| KR | 10-20090065778 A | 6/2009 |
| KR | 10-1266966 B1 | 5/2013 |
| KR | 10-2016-041632 A | 4/2016 |
| KR | 10-2016-0071127 A | 6/2016 |
| KR | 10-1675089 B1 | 11/2016 |
| TW | 480166 B | 3/2002 |
| WO | WO91/004713 A1 | 4/1991 |
| WO | WO92/03102 A1 | 3/1992 |
| WO | WO94/010935 A1 | 5/1994 |
| WO | WO96/23452 A1 | 8/1996 |
| WO | WO98/032394 A1 | 7/1998 |
| WO | WO98/044865 A1 | 10/1998 |
| WO | WO01/08592 A1 | 2/2001 |
| WO | WO01/85047 A2 | 11/2001 |
| WO | WO2002/017776 A2 | 3/2002 |
| WO | WO2002/062252 A1 | 8/2002 |
| WO | WO02/095475 A1 | 11/2002 |
| WO | WO03/003932 A2 | 1/2003 |
| WO | WO2006/096558 A2 | 9/2006 |
| WO | WO2006/100700 A1 | 9/2006 |
| WO | WO2006/133548 A1 | 12/2006 |
| WO | WO2007/019709 A2 | 2/2007 |
| WO | WO2007/071341 A1 | 6/2007 |
| WO | WO2007/103377 A2 | 9/2007 |
| WO | WO2008/115654 A1 | 9/2008 |
| WO | WO2009/016645 A2 | 2/2009 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/059988 A1 | 5/2010 |
| WO | WO2010/123892 A2 | 10/2010 |
| WO | WO2012/007003 A1 | 1/2012 |
| WO | WO2012/064684 A2 | 5/2012 |
| WO | WO2012/074304 A2 | 6/2012 |
| WO | WO2012/078980 A2 | 6/2012 |
| WO | WO2012/083968 A1 | 6/2012 |
| WO | WO2012/140021 A2 | 10/2012 |
| WO | WO2013/058879 A2 | 4/2013 |
| WO | WO2014/068107 A1 | 5/2014 |
| WO | WO2014/091865 A1 | 6/2014 |
| WO | WO2014/143911 A1 | 9/2014 |
| WO | WO2015/015289 A2 | 2/2015 |
| WO | WO2015/063032 A1 | 5/2015 |
| WO | WO2015/112638 A1 | 7/2015 |
| WO | WO2015/176004 A1 | 11/2015 |
| WO | WO2016/004415 A1 | 1/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | WO2016/113745 A1 | 7/2016 |
| WO | WO2016/116874 A1 | 7/2016 |
| WO | WO2016/200177 A1 | 12/2016 |
| WO | WO2017/006176 A1 | 1/2017 |
| WO | WO2017/182654 A1 | 10/2017 |
| WO | WO2018/057547 A1 | 3/2018 |
| WO | WO2018/085718 A2 | 5/2018 |
| WO | WO2018/232113 A1 | 12/2018 |
| WO | WO2019/018784 A1 | 1/2019 |

OTHER PUBLICATIONS

Farooq et al.; Relationship between tooth dimensions and malocclusion; JPMA: The Journal of the Pakistan Medical Association; 64(6); pp. 670-674; Jun. 2014.

Newcombe; DTAM: Dense tracking and mapping in real-time; 8 pages; retrieved from the internet (http://www.doc.ic.ac.uk/?ajd/Publications/newcombe_etal_iccv2011.pdf; on Dec. 2011.

ormco.com; Increasing clinical performance with 3D interactive treatment planning and patient-specific appliances; 8 pages; retrieved from the internet (http://www.konsident.com/wp-content/files_mf/1295385693http_ormco.com_index_cmsfilesystemaction_fileOrmcoPDF_whitepapers.pdf) on Feb. 27, 2019.

Video of DICOM to Surgical Guides; [Copy Not Enclosed], Can be viewed at <URL:https://youtu.be/47KtOmCEFQk; Published Apr. 4, 2016.

Sabina et al., U.S. Appl. No. 16/258,516 entitled "Diagnostic intraoral scanning" filed Jan. 25, 2019.

Sabina et al., U.S. Appl. No. 16/258,523 entitled "Diagnostic intraoral tracking" filed Jan. 25, 2019.

Sabina et al., U.S. Appl. No. 16/258,527 entitled "Diagnostic intraoral methods and apparatuses" filed Jan. 25, 2019.

Li et al.; U.S. Appl. No. 16/171,159 entitled "Alternative bite adjustment structures," filed Oct. 25, 2018.

Culp; U.S. Appl. No. 16/236,220 entitled "Laser cutting," filed Dec. 28, 2018.

Culp; U.S. Appl. No. 16/265,287 entitled "Laser cutting," filed Feb. 1, 2019.

(56) References Cited

OTHER PUBLICATIONS

Arakawa et al; Mouthguard biosensor with telemetry system for monitoring of saliva glucose: A novel cavitas sensor; Biosensors and Bioelectronics; 84; pp. 106-111; Oct. 2016.
O'Leary et al.; U.S. Appl. No. 16/195,701 entitled "Orthodontic retainers," filed Nov. 19, 2018.
Shanjani et al., U.S. Appl. No. 16/206,894 entitled "Sensors for monitoring oral appliances," filed Nov. 28, 2019.
Shanjani et al., U.S. Appl. No. 16/231,906 entitled "Augmented reality enhancements for dental practitioners." Dec. 24, 2018.
Kopleman et al., U.S. Appl. No. 16/220,381 entitled "Closed loop adaptive orthodontic treatment methods and apparatuses," Dec. 14, 2018.
Doruk et al.; The role of the headgear timer in extraoral co-operation; European Journal of Orthodontics; 26; pp. 289-291; Jun. 1, 2004.
Friedrich et al; Measuring system for in vivo recording of force systems in orthodontic treatment-concept and analysis of accuracy; J. Biomech .; 32(1); pp. 81-85; (Abstract Only) Jan. 1999.
Grest, Daniel; Marker-Free Human Motion Capture in Dynamic Cluttered Environments from a Single View-Point, PhD Thesis; 171 pages; Dec. 2007.
Invisalign; You were made to move. There's never been a better time to straighten your teeth with the most advanced clear aligner in the world; Product webpage; 2 pages; retrieved from the internet (www.invisalign.com/) on Dec. 28, 2017.
Kumar et al.; Rapid maxillary expansion: A unique treatment modality in dentistry; J. Clin. Diagn. Res.; 5(4); pp. 906-911; Aug. 2011.
Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-1471; Dec. 2014.
Sahm et al.; "Micro-Electronic Monitoring of Functional Appliance Wear"; Eur J Orthod.; 12(3); pp. 297-301; Aug. 1990.
Sahm; Presentation of a wear timer for the clarification of scientific questions in orthodontic orthopedics; Fortschritte der Kieferorthopadie; 51 (4); pp. 243-247; (Translation Included) Jul. 1990.
Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.
Thera Mon; "Microsensor"; 2 pages; retrieved from the internet (www.english.thera-mon.com/the-product/transponder/index.html); on Sep. 19, 2016.
Wikipedia; Palatal expansion; 3 pages; retrieved from the internet (https://en.wikipedia.org/wiki/Palatal_expansion) on Mar. 5, 2018.
Wireless Sensor Networks Magazine; Embedded Teeth for Oral Activity Recognition; 2 pages; retrieved on Sep. 19, 2016 from the internet (www.wsnmagazine.com/embedded-teeth/); Jul. 29, 2013.
Witt et al.; The wear-timing measuring device in orthodontics-cui bono? Reflections on the state-of-the-art in wear-timing measurement and compliance research in orthodontics; Fortschr Kieferorthop .; 52(3); pp. 117-125; (Translation Included) Jun. 1991.
Yamada et al.; Simulation of fan-beam type optical computed-tomography imaging of strongly scattering and weakly absorbing media; Applied Optics; 32(25); pp. 4808-4814; Sep. 1, 1993.
Grove et al.; U.S. Appl. No. 15/726,243 entitled "Interproximal reduction templates," filed Oct. 5, 2017.
Cramer et al.; U.S. Appl. No. 15/942,341 entitled "Orthodontic appliances including at least partially un-erupted teeth and method of forming them," filed Mar. 30, 2018.
Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.
Alves et al.; New trends in food allergens detection: toward biosensing strategies; Critical Reviews in Food Science and Nutrition; 56(14); pp. 2304-2319; doi: 10.1080/10408398.2013.831026; Oct. 2016.
CSI Computerized Scanning and Imaging Facility; What is a maximum/minimum intensity projection (MIP/MinIP); 1 page; retrived from the internet (http://csi.whoi.edu/content/what-maximumminimum-intensity-projection-mipminip); Jan. 4, 2010.
Di Muzio et al.; Minimum intensity projection (MinIP); 6 pages; retrieved from the internet (https://radiopaedia.org/articles/minimum-intensity-projection-minip) on Sep. 6, 2018.
Ellias et al.; Proteomic analysis of saliva identifies potential biomarkers for orthodontic tooth movement; The Scientific World Journal; vol. 2012; Article ID 647240; dio:10.1100/2012/647240; 7 pages; (year of pub. sufficiently earlier than effective US filing date and any foreign priority date) 2012.
Florez-Moreno; Time-related changes in salivary levels of the osteotropic factors sRANKL and OPG through orthodontic tooth movement; American Journal of Orthodontics and Dentofacial Orthopedics; 143(1); pp. 92-100; Jan. 2013.
Sirona Dental Systems GmbH, Cerec 3D, Manuel utilisateur, Version 2.0X (in French); 114 pages; (English translation of table of contents included); (year of pub. sufficiently earlier than effective US filing date and any foreign priority date); 2003.
Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.
Watson et al.; Pressures recorded at te denture base-mucosal surface interface in complete denture wearers; Journal of Oral Rehabilitation 14(6); pp. 575-589; Nov. 1987.
Wolf; Three-dimensional structure determination of semi-transparent objects from holographic data; Optics Communications; 1(4); pp. 153-156; Sep. 1969.
Riley et al.; U.S. Appl. No. 16/003,841 entitled Palatal expander with skeletal anchorage devices, filed Jun. 8, 2018.
Shanjani et al.; U.S. Appl. No. 16/019,037 entitled "Biosensor performance indicator for intraoral appliances," filed Jun. 26, 2018.
Sato et al.; U.S. Appl. No. 16/041,606 entitled "Palatal contour anchorage," filed Jul. 20, 2018.
Xue et al.; U.S. Appl. No. 16/010,087 entitled "Automatic detection of tooth type and eruption status," filed Jun. 15, 2018.
Sato et al.; U.S. Appl. No. 16/048,054 entitled "Optical coherence tomography for orthodontic aligners," filed Jul. 27, 2018.
Miller et al.; U.S. Appl. No. 16/038,088 entitled "Method and apparatuses for interactive ordering of dental aligners," filed Jul. 17, 2018.
Moalem et al.; U.S. Appl. No. 16/046,897 entitled Tooth shading, transparency and glazing, filed Jul. 26, 2018.
Nyukhtikov et al.; U.S. Appl. No. 15/998,883 entitled "Buccal corridor assessment and computation," filed Aug. 15, 2018.
Bandodkar et al.; All-printed magnetically self-healing electrochemical devices; Science Advances; 2(11); 11 pages; e1601465; Nov. 2016.
Bandodkar et al.; Self-healing inks for autonomous repair of printable electrochemical devices; Advanced Electronic Materials; 1(12); 5 pages; 1500289; Dec. 2015.
Bandodkar et al.; Wearable biofuel cells: a review; Electroanalysis; 28 (6); pp. 1188-1200; Jun. 2016.
Bandodkar et al.; Wearable chemical sensors: present challenges and future prospects; Acs Sensors; 1(5); pp. 464-482; May 11, 2016.
Imani et al.; A wearable chemical-electrophysiological hybrid biosensing system for real-time health and fitness monitoring; Nature Communications; 7; 11650. doi 1038/ncomms11650; 7 pages; May 23, 2016.
Jia et al.; Epidermal biofuel cells: energy harvesting from human perspiration; Angewandle Chemie International Edition; 52(28); pp. 7233-7236; Jul. 8, 2013.
Jia et al.; Wearable textile biofuel cells for powering electronics; Journal of Materials Chemistry A; 2(43); pp. 18184-18189; Oct. 14, 2014.
Jeerapan et al.; Stretchable biofuel cells as wearable textile-based self-powered sensors; Journal of Materials Chemistry A; 4(47); pp. 18342-18353; Dec. 21, 2016.
Kim et al.; Advanced materials for printed wearable electrochemical devices: A review; Advanced Electronic Materials; 3(1); 15 pages; 1600260; Jan. 2017.

(56) References Cited

OTHER PUBLICATIONS

Kim et al.; Noninvasive alcohol monitoring using a wearable tatto-based iontophoretic-biosensing system; Acs Sensors; 1(8); pp. 1011-1019; Jul. 22, 2016.

Kim et al.; Non-invasive mouthguard biosensor for continuous salivary monitoring of metabolites; Analyst; 139(7); pp. 1632-1636; Apr. 7, 2014.

Kim et al.; A wearable fingernail chemical sensing platform: pH sensing at your fingertips; Talanta; 150; pp. 622-628; Apr. 2016.

Kim et al.; Wearable salivary uric acid mouthguard biosensor with integrated wireless electronics; Biosensors and Bioelectronics; 74; pp. 1061-1068; 19 pages; (Author Manuscript); Dec. 2015.

Kumar et al.; All-printed, stretchable Zn—Ag20 rechargeable battery via, hyperelastic binder for self-powering wearable electronics; Advanced Energy Materials; 7(8); 8 pages; 1602096; Apr. 2017.

Kumar et al.; Biomarkers in orthodontic tooth movement; Journal of Pharmacy Bioallied Sciences; 7(Suppl 2); pp. S325-S330; 12 pages; (Author Manuscript); Aug. 2015.

Parrilla et al.; A textile-based stretchable multi-ion potentiometric sensor; Advanced Healthcare Materials; 5(9); pp. 996-1001; May 2016.

Windmiller et al.; Wearable electrochemical sensors and biosensors: a review; Electroanalysis; 25(1); pp. 29-46; Jan. 2013.

Zhou et al.; Bio-logic analysis of injury biomarker patterns in human serum samples; Talanta; 83(3); pp. 955-959; Jan. 15, 2011.

Zhou et al.; Biofuel cells for self-powered electrochemical biosensing and logic biosensing: A review; Electroanalysis; 24(2); pp. 197-209; Feb. 2012.

Kopelman et al.; U.S. Appl. No. 16/152,281 entitled "Intraoral appliances for sampling soft-tissue," filed Oct. 4, 2018.

Morton et al.; U.S. Appl. No. 16/177,067 entitled "Dental appliance having selective occlusal loading and controlled intercuspation," filed Oct. 31, 2018.

Akopov et al.; U.S. Appl. No. 16/178,491 entitled "Automatic treatment planning," filed Nov. 1, 2018.

Elbaz et al.; U.S. Appl. No. 16/198,488 entitled "Intraoral scanner with dental diagnostics capabilities," filed Nov. 21, 2018.

Elbaz et al.; U.S. Appl. No. 16/188,262 entitled "Intraoral scanner with dental diagnostics capabilities," filed Nov. 12, 2018.

Bernabe et al.; Are the lower incisors the best predictors for the unerupted canine and premolars sums? An analysis of peruvian sample; The Angle Orthodontist; 75(2); pp. 202-207; Mar. 2005.

Collins English Dictionary; Teeth (definition); 9 pages; retrieved from the internet (https:www.collinsdictionary.com/us/dictionary/english/teeth) on May 13, 2019.

Dental Monitoring; Basics: How to put the cheek retractor ?; 1 page (Screenshot); retrieved from the interenet (https://www.youtube.com/watch?v=6K1HXw4Kq3c); May 27, 2016.

Dental Monitoring; Dental monitoring tutorial; 1 page (Screenshot); retrieved from the internet (https:www.youtube.com/watch?v=Dbe3udOf9_c); Mar. 18, 2015.

dictionary.com; Plural (definition); 6 pages; retrieved from the internet ( https://www.dictionary.com/browse/plural#) on May 13, 2019.

dictionary.com; Quadrant (definition); 6 pages; retrieved from the internet ( https://www.dictionary.com/browse/quadrant?s=t) on May 13, 2019.

Ecligner Selfie; Change your smile; 1 page (screenshot); retrieved from the internet (https:play.google.com/store/apps/details?id=parklict.ecligner); on Feb. 13, 2018.

Martinelli et al.; Prediction of lower permanent canine and premolars width by correlation methods; The Angle Orthodontist; 75(5); pp. 805-808; Sep. 2005.

Nourallah et al.; New regression equations for predicating the size of unerupted canines and premolars in a contemporary population; The Angle Orthodontist; 72(3); pp. 216-221; Jun. 2002.

Paredes et al.; A new, accurate and fast digital method to predict unerupted tooth size; The Angle Orthodontist; 76(1); pp. 14-19; Jan. 2006.

Levin; U.S. Appl. No. 16/282,431 entitled "Estimating a surface texture of a tooth," filed Feb. 2, 2019.

AADR. American Association for Dental Research; Summary of Activities; Los Angeles, CA; p. 195; Mar. 20-23,(year of pub. sufficiently earlier than effective US filing date and any foreign priority date) 1980.

Alcaniz et al.; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.

Alexander et al.; The DigiGraph Work Station Part 2 Clinical Management; J. Clin. Orthod.; pp. 402-407; (Author Manuscript); Jul. 1990.

Allesee Orthodontic Appliance: Important Tip About Wearing the Red White & Blue Active Clear Retainer System; Allesee Orthodontic Appliances-Pro Lab; 1 page; (year of pub. sufficiently earlier than effective US filing date and any foreign priority date); 1998.

Allesee Orthodontic Appliances: DuraClearTM; Porduct information; 1 page; (year of pub. sufficiently earlier than effective US filing date and any foreign priority date) 1997.

Allesee Orthodontic Appliances; The Choice Is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.

Allesee Orthodontic Appliances; The Choice Is Clear: Red, White & Blue . . . The Simple, Affordable, No-Braces Treatment; p(roduct information), 6 pages; (year of pub. sufficiently earlier than effective US filing date and any foreign priority date) 2003.

Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.

Allesee Orthodontic Appliances; The Red, White & Blue Way to Improve Your Smile; (information for patients), 2 pages; (year of pub. sufficiently earlier than effective US filing date and any foreign priority date) 1992.

Allesee Orthodontic Appliances; You may be a candidate for this invisible no-braces treatment; product information for patients; 2 pages; (year of pub. sufficiently earlier than effective US filing date and any foreign priority date) 2002.

Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.

Altschuler et al.; Laser Electro-Optic System for Rapid Three-Dimensional (3D) Topographic Mapping of Surfaces; Optical Engineering; 20(6); pp. 953-961; Dec. 1981.

Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.

Altschuler; 3D Mapping of Maxillo-Facial Prosthesis; AADR Abstract #607; 2 pages total, (year of pub. sufficiently earlier than effective US filing date and any foreign priority date) 1980.

Andersson et al.; Clinical Results with Titanium Crowns Fabricated with Machine Duplication and Spark Erosion; Acta Odontologica Scandinavica; 47(5); pp. 279-286; Oct. 1989.

Andrews, The Six Keys to Optimal Occlusion Straight Wire, Chapter 3, L.A. Wells; pp. 13-24; (year of pub. sufficiently earlier than effective US filing date and any foreign priority date) 1989.

Barone et al.; Creation of 3D multi-body orthodontic models by using independent imaging sensors; Sensors; 13(2); pp. 2033-2050; Feb. 5, 2013.

Bartels et al.; An Introduction to Splines for Use in Computer Graphics and Geometric Modeling; Morgan Kaufmann Publishers; pp. 422-425 Jan. 1, 1987.

(56) References Cited

OTHER PUBLICATIONS

Baumrind et al., "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.
Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
Begole et al.; A Computer System for the Analysis of Dental Casts; The Angle Orthodontist; 51(3); pp. 252-258; Jul. 1981.
Bernard et al.; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.
Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biggerstaff; Computerized Diagnostic Setups and Simulations; Angle Orthodontist; 40(I); pp. 28-36; Jan. 1970.
Biostar Operation & Training Manual. Great Lakes Orthodontics, Ltd. 199 Fire Tower Drive, Tonawanda, New York. 14150-5890, 20 pages; (year of pub. sufficiently earlier than effective US filing date and any foreign priority date) 1990.
Blu et al.; Linear interpolation revitalized; IEEE Transactions on Image Processing; 13(5); pp. 710-719; May 2004.
Bourke, Coordinate System Transformation; 1 page; retrived from the internet (http://astronomy.swin.edu.au/' pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on the Uses of the Computer in Orthodontic Practice (Part 1); Journal of Clinical Orthodontics; 13(7); pp. 442-453; (interview); Jul. 1979.
Burstone; Dr. Charles J. Burstone on the Uses of the Computer in Orthodontic Practice (Part 2); journal of Clinical Orthodontics; 13(8); pp. 539-551 (interview); Aug. 1979.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.

Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
Cottingham; Gnathologic Clear Plastic Positioner; American Journal of Orthodontics; 55(1); pp. 23-31; Jan. 1969.
Crawford; CAD/CAM in the Dental Office: Does It Work ?; Canadian Dental Journal; 57(2); pp. 121-123 Feb. 1991.
Crawford; Computers in Dentistry: Part 1: CAD/CAM: The Computer Moves Chairside, Part 2: F. Duret A Man With a Vision, Part 3: The Computer Gives New Vision—Literally, Part 4: Bytes 'N Bites the Computer Moves From the Front Desk to the Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
Cureton; Correcting Malaligned Mandibular Incisors with Removable Retainers; Journal of Clinical Orthodontics; 30(7); pp. 390-395; Jul. 1996.
Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
DCS Dental AG; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.
Dent-x; Dentsim . . . Dent-x's virtual reality 3-D training simulator . . . A revolution in dental education; 6 pages; retrieved from the internet (http://www.dent-x.com/DentSim.htm); on Sep. 24, 1998.
Doyle; Digital Dentistry; Computer Graphics World; pp. 50-52 andp. 54; Oct. 2000.
Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.
Duret et al.; CAD/CAM Imaging in Dentistry; Current Opinion in Dentistry; 1 (2); pp. 150-154; Apr. 1991.
Duret et al.; CAD-CAM in Dentistry; Journal of the American Dental Association; 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides; The Microcomputer in the Orthodontic Office; Journal of Clinical Orthodontics; 13(11); pp. 767-772; Nov. 1979.
Elsasser; Some Observations on the History and Uses of the Kesling Positioner; American Journal of Orthodontics; 36(5); pp. 368-374; May 1, 1950.
English translation of Japanese Laid-Open Publication No. 63-11148 to inventor T. Ozukuri (Laid-Open on Jan. 18, 1998) pp. 1-7.
Faber et al.; Computerized Interactive Orthodontic Treatment Planning; American Journal of Orthodontics; 73(1); pp. 36-46; Jan. 1978.
Felton et al.; A Computerized Analysis of the Shape and Stability of Mandibular Arch Form; American Journal of Orthodontics and Dentofacial Orthopedics; 92(6); pp. 478-483; Dec. 1987.
Friede et al.; Accuracy of Cephalometric Prediction in Orthognathic Surgery; Journal of Oral and Maxillofacial Surgery; 45(9); pp. 754-760; Sep. 1987.

(56) References Cited

OTHER PUBLICATIONS

Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf); on Aug. 21, 2018.

Gao et al.; 3-D element Generation for Multi-Connected Complex Dental and Mandibular Structure; IEEE Proceedings International Workshop in Medical Imaging and Augmented Reality; pp. 267-271; Jun. 12, 2001.

Gim-Alldent Deutschland, "Das DUX System: Die Technik," 3 pages; (English Translation Included); (year of pub. sufficiently earlier than effective US filing date and any foreign priority date); 2002.

Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.

Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.

Guess et al.; Computer Treatment Estimates In Orthodontics and Orthognathic Surgery; Journal of Clinical Orthodontics; 23(4); pp. 262-268; 11 pages; (Author Manuscript); Apr. 1989.

Heaven et al.; Computer-Based Image Analysis of Artificial Root Surface Caries; Abstracts of Papers #2094; Journal of Dental Research; 70:528; (Abstract Only); Apr. 17-21, 1991.

Highbeam Research; Simulating stress put on jaw. (ANSYS Inc.'s finite element analysis software); 2 pages; retrieved from the Internet (http://static.highbeam.eom/t/toolingampproduction/november011996/simulatingstressp utonfa . . . ); on Nov. 5, 2004.

Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Inclused); Feb. 1987.

Hoffmann et al.; Role of Cephalometry for Planning of Jaw Orthopedics and Jaw Surgery Procedures; Informatbnen, pp. 375-396; (English Abstract Included); Mar. 1991.

Hojjatie et al.; Three-Dimensional Finite Element Analysis of Glass-Ceramic Dental Crowns; Journal of Biomechanics; 23(11); pp. 1157-1166; Jan. 1990.

Huckins; CAD-CAM Generated Mandibular Model Prototype from MRI Data; AAOMS, p. 96; (Abstract Only); (year of pub. sufficiently earlier than effective US filing date and any foreign priority date) 1999.

JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.

JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.

Jerrold; The Problem, Electronic Data Transmission and the Law; American Journal of Orthodontics and Dentofacial Orthopedics; 113(4); pp. 478-479; 5 pages; (Author Manuscript); Apr. 1998.

Jones et al.; An Assessment of the Fit of a Parabolic Curve to Pre- and Post-Treatment Dental Arches; British Journal of Orthodontics; 16(2); pp. 85-93; May 1989.

Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.

Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.

Kanazawa et al.; Three-Dimensional Measurements of the Occlusal Surfaces of Upper Molars in a Dutch Population; Journal of Dental Research; 63(11); pp. 1298-1301; Nov. 1984.

Kesling et al.; The Philosophy of the Tooth Positioning Appliance; American Journal of Orthodontics and Oral surgery; 31(6); pp. 297-304; Jun. 1945.

Kesling; Coordinating the Predetermined Pattern and Tooth Positioner with Conventional Treatment; American Journal of Orthodontics and Oral Surgery; 32(5); pp. 285-293; May 1946.

Kleeman et al.; The Speed Positioner; J. Clin. Orthod.; 30(12); pp. 673-680; Dec. 1996.

Kochanek; Interpolating Splines with Local Tension, Continuity and Bias Control; Computer Graphics; 18(3); pp. 33-41; Jan. 1, 1984.

Kunii et al.; Articulation Simulation for an Intelligent Dental Care System; Displays; 15(3); pp. 181-188; Jul. 1994.

Kuroda et al.; Three-Dimensional Dental Cast Analyzing System Using Laser Scanning; American Journal of Orthodontics and Dentofacial Orthopedics; 110(4); pp. 365-369; Oct. 1996.

Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.

Leinfelder et al.; A New Method for Generating Ceramic Restorations: a CAD-CAM System; Journal of the American Dental Association; 118(6); pp. 703-707; Jun. 1989.

Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.

McCann; Inside the ADA; J. Amer. Dent. Assoc, 118:286-294; Mar. 1989.

McNamara et al.; Invisible Retainers; J. Clin Orthod.; pp. 570-578; 11 pages; (Author Manuscript); Aug. 1985.

McNamara et al.; Orthodontic and Orthopedic Treatment in the Mixed Dentition; Needham Press; pp. 347-353; Jan. 1993.

Moermann et al., Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.

Moles; Correcting Mild Malalignments—As Easy as One, Two, Three; AOA/Pro Corner; 11(2); 2 pages; (year of pub. sufficiently earlier than effective US filing date and any foreign priority date) 2002.

Mormann et al.; Marginale Adaptation von adhasuven Porzellaninlays in vitro; Separatdruck aus:Schweiz. Mschr. Zahnmed.; 95; pp. 1118-1129; 8 pages; (Macine Translated English Abstract); (year of pub. sufficiently earlier than effective US filing date and any foreign priority date); 1985.

Nahoum; The Vacuum Formed Dental Contour Appliance; N. Y. State Dent. J.; 30(9); pp. 385-390; Nov. 1964.

Nash; CEREC CAD/CAM Inlays: Aesthetics and Durability in a Single Appointment; Dentistry Today; 9(8); pp. 20, 22-23 and 54; Oct. 1990.

Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.

Ogawa et al.; Mapping, profiling and clustering of pressure pain threshold (PPT) in edentulous oral muscosa; Journal of Dentistry; 32(3); pp. 219-228; Mar. 2004.

Ogimoto et al.; Pressure-pain threshold determination in the oral mucosa; Journal of Oral Rehabilitation; 29(7); pp. 620-626; Jul. 2002.

Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.

Pinkham; Foolish Concept Propels Technology; Dentist, 3 pages , Jan./Feb. 1989.

(56) References Cited

OTHER PUBLICATIONS

Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 Abstract Collection; 23 pages; (year of pub. sufficiently earlier than effective US filing date and any foreign priority date) 1993.
Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & Ars Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art ?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of the PAR Index (Peer Assessment Rating): Reliability and Validity.; The European Journal of Orthodontics; 14(2); pp. 125-139; Apr. 1992.
Richmond et al.; The Development of a 3D Cast Analysis System; British Journal of Orthodontics; 13(1); pp. 53-54; Jan. 1986.
Richmond; Recording The Dental Cast In Three Dimensions; American Journal of Orthodontics and Dentofacial Orthopedics; 92(3); pp. 199-206; Sep. 1987.
Rudge; Dental Arch Analysis: Arch Form, A Review of the Literature; The European Journal of Orthodontics; 3(4); pp. 279-284; Jan. 1981.
Sakuda et al.; Integrated Information-Processing System In Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al.; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.

Shimada et al.; Application of optical coherence tomography (OCT) for diagnosis of caries, cracks, and defects of restorations; Current Oral Health Reports; 2(2); pp. 73-80; Jun. 2015.
Siemens; CEREC—Computer-Reconstruction, High Tech in der Zahnmedizin; 15 pagesl; (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.
Sturman; Interactive Keyframe Animation of 3-D Articulated Models; Proceedings Graphics Interface '84; vol. 86; pp. 35-40; May-Jun. 1984.
The American Heritage, Stedman's Medical Dictionary; Gingiva; 3 pages; retrieved from the interent (http://reference.com/search/search?q=gingiva) on Nov. 5, 2004.
The Dental Company Sirona: Cerc omnicam and cerec bluecam brochure: The first choice in every case; 8 pages; (year of pub. sufficiently earlier than effective US filing date and any foreign priority date) 2014.
Thorlabs; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-28; Sep.-Oct. 1992.
Tru-Tatn Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Van Der Linden et al.; Three-Dimensional Analysis of Dental Casts by Means of the Optocom; Journal of Dental Research; 51(4); p. 1100; Jul.-Aug. 1972.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Van Hilsen et al.; Comparing potential early caries assessment methods for teledentistry; BMC Oral Health; 13(16); doi: 10.1186/1472-6831-13-16; 9 pages; Mar. 2013.
Varady et al.; Reverse Engineering of Geometric Models an Introduction; Computer-Aided Design; 29(4); pp. 255-268; 20 pages; (Author Manuscript); Apr. 1997.
Verstreken et al.; An Image-Guided Planning System for Endosseous Oral Implants; IEEE Transactions on Medical Imaging; 17(5); pp. 842-852; Oct. 1998.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek et.al.; Clinical Use of Silicone Elastomer Applicances; JCO; 23(10); pp. 694-700; Oct. 1989.
Wells; Application of the Positioner Appliance in Orthodontic Treatment; American Journal of Orthodontics; 58(4); pp. 351-366; Oct. 1970.
Williams; Dentistry and CAD/CAM: Another French Revolution; J. Dent. Practice Admin.; 4(1); pp. 2-5 Jan./Mar. 1987.

(56) References Cited

OTHER PUBLICATIONS

Williams; The Switzerland and Minnesota Developments in CAD/CAM; Journal of Dental Practice Administration; 4(2); pp. 50-55; Apr./Jun. 1987.
Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
beautyworlds.com; Virtual plastic surgery—beautysurge.com announces launch of cosmetic surgery digital imaging services; 5 pages; retrieved from the internet (http://www.beautyworlds.com/cosmossurgdigitalimagning.htm); Mar. 2004.
Berland; The use of smile libraries for cosmetic dentistry; Dental Tribunne: Asia pacfic Edition; pp. 16-18; Mar. 29, 2006.
Bookstein; Principal warps: Thin-plate splines and decomposition of deformations; IEEE Transactions on pattern analysis and machine intelligence; 11(6); pp. 567-585; Jun. 1989.
Cadent Inc.; OrthoCAD ABO user guide; 38 pages; Dec. 21, 2005.
Cadent Inc.; Reviewing and modifying an orthoCAD case; 4 pages; Feb. 14, 2005.
Daniels et al.; The development of the index of complexity outcome and need (ICON); British Journal of Orthodontics; 27(2); pp. 149-162; Jun. 2000.
Dentrix; Dentrix G3, new features; 2 pages; retrieved from the internet (http://www.dentrix.com/g3/new_features/index.asp); on Jun. 6, 2008.
Di Giacomo et al.; Clinical application of sterolithographic surgical guides for implant placement: Preliminary results; Journal Periodontolgy; 76(4); pp. 503-507; Apr. 2005.
Gansky; Dental data mining: potential pitfalls and practical issues; Advances in Dental Research; 17(1); pp. 109-114; Dec. 2003.

Geomagic; Dental reconstruction; 1 page; retrieved from the internet (http://geomagic.com/en/solutions/industry/detal_desc.php) on Jun. 6, 2008.
Gottschalk et al.; OBBTree: A hierarchical structure for rapid interference detection; 12 pages; (http://www.cs.unc.edu/?geom/OBB/OBBT.html); retrieved from te internet (https://www.cse.iitk.ac.in/users/amit/courses/RMP/presentations/dslamba/presentation/sig96.pdf) on Apr. 25, 2019.
gpsdentaire.com; Get a realistic smile simulation in 4 steps with GPS; a smile management software; 10 pages; retrieved from the internet (http://www.gpsdentaire.com/en/preview/) on Jun. 6, 2008.
Karaman et al.; A practical method of fabricating a lingual retainer; Am. Journal of Orthodontic and Dentofacial Orthopedics; 124(3); pp. 327-330; Sep. 2003.
Mantzikos et al.; Case report: Forced eruption and implant site development; The Angle Orthodontist; 68(2); pp. 179-186; Apr. 1998.
Methot; Get the picture with a gps for smile design in 3 steps; Spectrum; 5(4); pp. 100-105; (year of pub. sufficiently earlier than effective US filing date and any foreign priority date) 2006.
OrthoCAD downloads; retrieved Jun. 27, 2012 from the internet (www.orthocad.com/download/downloads.asp); 2 pages; Feb. 14, 2005.
Page et al.; Validity and accuracy of a risk calculator in predicting periodontal disease; Journal of the American Dental Association; 133(5); pp. 569-576; May 2002.
Patterson Dental; Cosmetic imaging; 2 pages retrieved from the internet (http://patterson.eaglesoft.net/cnt_di_cosimg.html) on Jun. 6, 2008.
Rose et al.; The role of orthodontics in implant dentistry; British Dental Journal; 201(12); pp. 753-764; Dec. 23, 2006.
Rubin et al.; Stress analysis of the human tooth using a three-dimensional finite element model; Journal of Dental Research; 62(2); pp. 82-86; Feb. 1983.
Sarment et al.; Accuracy of implant placement with a sterolithographic surgical guide; journal of Oral and Maxillofacial Implants; 118(4); pp. 571-577; Jul. 2003.
Smalley; Implants for tooth movement: Determining implant location and orientation: Journal of Esthetic and Restorative Dentistry; 7(2); pp. 62-72; Mar. 1995.
Smart Technology; Smile library II; 1 page; retrieved from the internet (http://smart-technology.net/) on Jun. 6, 2008.
Smile-Vision_The smile-vision cosmetic imaging system; 2 pages; retrieved from the internet (http://www.smile-vision.net/cos_imaging.php) on Jun. 6, 2008.
Szeliski; Introduction to computer vision: Structure from motion; 64 pages; retrieved from the internet (http://robots.stanford.edu/cs223b05/notes/CS%20223-B%20L10%structurefrommotion1b.ppt, on Feb. 3, 2005.
Vevin et al.; Pose estimation of teeth through crown-shape matching; In Medical Imaging: Image Processing of International Society of Optics and Photonics; vol. 4684; pp. 955-965; May 9, 2002.
Virtual Orthodontics; Our innovative software; 2 pages; (http://www.virtualorthodontics.com/innovativesoftware.html); retrieved from the internet (https://web.archive.org/web/20070518085145/http://www.virtualorthodontics.com/innovativesoftware.html); (year of pub. sufficiently earlier than effective US filing date and any foreign priority date) 2005.
Wiedmann; According to the laws of harmony to find the right tooth shape with assistance of the computer; Digital Dental News; 2nd Vol.; pp. 0005-0008; (English Version Included); Apr. 2008.
Wong et al.; Computer-aided design/computer-aided manufacturing surgical guidance for placement of dental implants: Case report; Implant Dentistry; 16(2); pp. 123-130; Sep. 2007.
Wong et al.; The uses of orthodontic study models in diagnosis and treatment planning; Hong Knog Dental Journal; 3(2); pp. 107-115; Dec. 2006.
Yaltara Software; Visual planner; 1 page; retrieved from the internet (http://yaltara.com/vp/) on Jun. 6, 2008.
Zhang et al.; Visual speech features extraction for improved speech recognition; 2002 IEEE International conference on Acoustics, Speech and Signal Processing; vol. 2; 4 pages; May 13-17, 2002.

(56) References Cited

OTHER PUBLICATIONS

Arnone et al.; U.S. Appl. No. 16/235,449 entitled "Method and system for providing indexing and cataloguing of orthodontic related treatment profiles and options," filed Dec. 28, 2018.
Mason et al.; U.S. Appl. No. 16/374,648 entitled "Dental condition evaluation and treatment," filed Apr. 3, 2019.
Brandt et al.; U.S. Appl. No. 16/235,490 entitled "Dental wire attachment," filed Dec. 28, 2018.
Kou; U.S. Appl. No. 16/270,891 entitled "Personal data file," filed Feb. 8, 2019.

* cited by examiner

```
┌─────────────────────────────────────────────────────────────────────┐
│     Input an initial anterior leveling dataset of the patient's anterior teeth  │
│                                   101                                │
└─────────────────────────────────────────────────────────────────────┘
                                    ▼
┌─────────────────────────────────────────────────────────────────────┐
│  Input an incisor preference ($b_{pref}$) from the doctor regarding a leveling position of lateral │
│  incisors (e.g., with respect to leveling position of central incisors). Incisor preference may │
│       optionally indicate position of lateral incisors relative to central incisors.  │
│                                   103                                │
└─────────────────────────────────────────────────────────────────────┘
                                    ▼
┌─────────────────────────────────────────────────────────────────────┐
│     Obtain an average anterior leveling ($\mu$) dataset derived from a plurality of patients │
│                                   105                                │
└─────────────────────────────────────────────────────────────────────┘
                                    ▼
┌─────────────────────────────────────────────────────────────────────┐
│  Determine a final leveling dataset based on the initial anterior leveling dataset, the incisor │
│  preference received from the doctor and the average anterior leveling dataset (optionally, may │
│  include latent factor such as country bias, gender bias, doctor/gender bias, etc.). Optionally, │
│    may use matrix factroization. The final leveling dataset may include possible leveling │
│             recommendations and a score for each leveling recommendation.  │
│                                   107                                │
└─────────────────────────────────────────────────────────────────────┘
                                    ▼
┌─────────────────────────────────────────────────────────────────────┐
│  Optionally, select the final leveling recommendation from the final leveling dataset (e.g., the │
│      set having the highest score from the set of possible leveling recommendations) │
│                                   109                                │
└─────────────────────────────────────────────────────────────────────┘
                                    ▼
┌─────────────────────────────────────────────────────────────────────┐
│  Optionally, adding the final leveling recommendation to the average anterior leveling dataset │
│                                   111                                │
└─────────────────────────────────────────────────────────────────────┘
                                    ▼
┌─────────────────────────────────────────────────────────────────────┐
│    Optionally, determining a posterior leveling dataset based on the patient's posterior teeth │
│    (e.g., determining the dataset by determining the final leveling data set based on the initial │
│  anterior leveling dataset, the incisor preference received from the doctor, the average anterior │
│                  leveling dataset, and the posterior leveling dataset) │
│                                   113                                │
└─────────────────────────────────────────────────────────────────────┘
                                    ▼
┌─────────────────────────────────────────────────────────────────────┐
│   Display (e.g., to the doctor) a final leveling recommendation from the final leveling dataset, │
│              and/or generate an orthodontic device from the leveling dataset │
│                                   115                                │
└─────────────────────────────────────────────────────────────────────┘
```

FIG. 1E

APPARATUSES AND METHODS ASSISTING IN DENTAL THERAPIES

CROSS REFERENCE TO RELATED APPLICATIONS

This application claims the benefit of priority to U.S. Provisional Application No. 62/477,389, filed Mar. 27, 2017, which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Orthodontic procedures typically involve repositioning a patient's teeth to a desired arrangement in order to correct malocclusions and/or improve aesthetics. To achieve these objectives, orthodontic appliances such as braces, shell aligners, and the like can be applied to the patient's teeth by an orthodontic practitioner and/or by the patients themselves. The appliance can be configured to exert force on one or more teeth in order to effect desired tooth movements according to a treatment plan.

Orthodontic aligners may include devices that are removable and/or replaceable over the teeth. Orthodontic aligners may be provided as part of an orthodontic treatment plan. In some orthodontic treatment plans involving removable and/or replaceable aligners, a patent may be provided plurality of orthodontic aligners over the course of treatment to make incremental position adjustments to the patient's teeth. An orthodontic aligner may have a polymeric trough with an inner cavity shaped to receive and resiliently reposition teeth from one tooth arrangement to a successive tooth arrangement. Orthodontic aligners may include "active" regions that impose repositioning forces on teeth and "passive" regions that retain teeth in their current state.

Many orthodontic treatment plans, including at least some of those that involve removable and/or replaceable appliances that provide incremental forces on teeth over time, include a determination of tooth leveling. Tooth leveling may involve the extent to which a person's teeth are intruded or extruded relative to their gums. Under many orthodontic treatment plans, tooth leveling may be determined independently of other aspects of determination of final position(s) of a patient's teeth. Some factors influencing tooth leveling are aesthetics (which, in many orthodontic treatment plans may primarily affect anterior tooth positioning) and clinical positioning (which may primarily affect posterior teeth). A tooth leveling determination may also depend on what a given doctor thinks is appropriate for a patient as well as characteristics of the patient (patient gender, patient heritage, patent location, etc.). Existing systems do not effectively provide a treatment professional with recommendations of tooth levels appropriate for a patient, much less offer treatment professionals the ability to design orthodontic appliances to accommodate and/or visualize the effects of tooth level recommendations.

SUMMARY

Systems, methods, and/or computer-readable media described herein provide technical solutions to the highly technical problems of machine visualization of tooth leveling recommendations. "Tooth leveling," as used herein, may refer to a parameter for identifying the extent a tooth is intruded and/or extruded from a patient's gums. Tooth leveling may be achieved by a variety of ways, including application of incremental forces to a tooth over a specified period of time. Tooth leveling may generally refer to adjusting/modifying the position (e.g., the z-component of position) of a tooth or teeth. Tooth leveling may include anterior leveling (e.g., leveling of the anterior teeth, e.g., incisors and canines), posterior leveling (e.g., leveling of posterior teeth, e.g., premolars and molars, and/or arch shape. The methods and apparatuses described herein may include one or more of: anterior leveling, posterior leveling or arch shape adjustment. Thus, "tooth leveling" may refer to one or more of these (in combination). In some variations, it may be beneficial to separately perform methods for anterior leveling and posterior leveling of teeth; as mentioned, a recommendation for tooth leveling may include both anterior tooth leveling and posterior tooth leveling (and/or arch shape) or it may include just one or two of these.

Systems, methods, and/or computer-readable media explored herein train automated agents to learn latent leveling factors to associate one or more specific leveling recommendations with specific patient types. An "automated agent," as used herein, may refer to one or more computer-program instructions, which when accessed by a computer processor, execute one or more computer-implemented methods without human intervention.

A "latent leveling factor," as used herein, may refer to a factor, unknown at the time of training, that forms the basis of a significant association between specific treatment professional(s) and specific historical leveling recommendations those treatment professional(s) have provided to patients. A "latent leveling factor," in some implementations, may also refer to a factor, unknown at the time of training that forms the basis of a significant association between specific patient type and specific historical leveling recommendations for that patient type. A "leveling recommendation," as used herein, may refer to a recommended tooth leveling provided to a patient as part of a prescription. A "historical leveling recommendation," as used herein, may refer to a leveling recommendation that was implemented on a specific patient and/or group of patients. A historical leveling recommendation may be contrasted with an "estimated" or "derived" leveling recommendation that is to be prescribed to a patient. A "patient type," as used herein, may refer to a characteristic (gender, country of origin, age, jaw parameter range, face parameter range, arch parameter range, malocclusion characteristic, etc.) common to two or more patients. A "treatment professional," used interchangeably herein with "doctor," "orthodontist," "dentist," etc., may refer to any individual who implements a treatment plan, such as an orthodontic or restorative treatment plan.

In some implementations, a first set of historical leveling parameters are gathered. One or more of the first set of historical leveling parameters may be associated with a first set of treatment professionals. In some implementations, the first set of historical leveling parameters may include leveling parameters that the first set of treatment professionals have prescribed and/or implemented on a first set of patients. In various implementations, a second set of historical leveling parameters may be gathered. One or more of the second set of historical leveling parameters may be associated with a first set of patient types of patients who have undergone a treatment plan. The second set of historical leveling parameters may include leveling parameters implemented on the patent type of the first set of patients in the past.

A set of latent leveling factors may be derived from the first dataset and the second dataset. One or more of the latent leveling factors may provide a latent statistical basis (e.g., may be associated in a statistically significant way) to associate the first set of historical leveling parameters with the first set of doctors in the first dataset. One or more of the latent leveling factors may further provide a latent statistical basis to associate the second set of historical leveling parameters with the patient types of the first set of patients in the second dataset. Operations may be taken to regularize the set of latent leveling factors by, e.g., whether one or more of the latent leveling factors exceeds a complexity threshold, and removing any latent leveling factors exceeding the complexity threshold. Operations may also be taken to identify whether or not the one or more of the latent leveling factors correspond to bias by seeing if the latent leveling factors deviate from a known correlation between the first set of historic leveling parameters and the second set of historic leveling parameters.

The latent leveling factors may be used to derive a leveling recommendation for one or more combinations of doctors from the set of first doctors and one or more patient types from the one or more first set of patients. In some implementations, the latent leveling factors allow the combinations of doctor/patient type pairs to be associated with specific leveling recommendations. Advantageously, these latent leveling factors may be learned through training the automated agents described herein. One or more leveling recommendations may be stored in a leveling recommendation database as described further herein.

In various implementations, a leveling recommendation is identified for a specific patient as part of final dental position calculations and/or visualizations for that patient. The leveling recommendation may include recommended tooth levels for the outcome of an orthodontic prescription. The leveling recommendation may include specific parameters to identify the extent the patient's teeth will be extruded and/or intruded from their gums after the orthodontic treatment plan. The leveling recommendation may be provided in conjunction with, or independent of, other final dental position parameters, such as tooth location(s), orientation(s), etc.

In various implementations, the patient data may be associated with a doctor identifier of a doctor who is implementing the treatment plan. The doctor identifier may correspond to the specific doctor implementing the treatment plan or may correspond to one or more doctors who have provided prescriptions to other patients similarly situated to the patient.

In some implementations, patient data may be gathered. The patient data may include information about the patient's gender, country of origin, age, jaw parameter range, face parameter range, arch parameter range, malocclusion characteristic, etc. The patient data may be used to associate the patient with a patient type identifier. The patient type identifier may use one or more patient characteristics to group the patient with other patients who have undergone or will undergo orthodontic treatment. As an example, the patient type identifier may group the patient with other patients based on one or more of gender, country of origin, age, jaw parameter range, face parameter range, arch parameter range, malocclusion characteristic, etc.

The doctor identifier and the patient identifier may be used to identify a leveling recommendation for the patient. As noted herein, the leveling recommendation may be derived from one or more latent leveling factors using automated agents to learn those latent leveling factors based on historic leveling parameters used in historic populations of patients by historic populations of treatment professionals. The doctor and/or the patient may be provided with instructions to display the leveling recommendation in a format that is convenient to their orthodontic treatment plan(s). In various implementations, the leveling recommendations may be incorporated into one or more tooth positions displayed in treatment visualization software for the doctor and/or patient. As noted herein, the tooth positions may include and/or be compatible with tooth parameters, implicit ratings, vector ratings, multiple ratings for a patient, and/or a larger leveling model configured to be displayed on a computer to the doctor and/or the patient.

In general, described herein are methods and apparatuses (including systems, devices and software, hardware, and/or firmware) for providing recommendations, and in particular, recommendations that are tailored to a particular health care provider, for treating a particular patient. In particular, described herein a apparatuses and methods for providing a particular, specified health care provider with recommendation for orthodontic treatment, including leveling of one or more teeth. As used herein, a health care provider may refer to a physician, nurse, dentist, orthodontist, technician, etc., and may for the sake of simplicity be referred to herein as a "doctor".

In some embodiments, anterior tooth leveling may generally include creating a model based on known or assumed factors regarding doctors and patients and then capturing the residual error using a factorized matrix. This may provide an accurate prediction for anterior leveling that should be desirable to the specific doctor being provided with the recommendation. Similarly, posterior leveling may generally include analysis of previous cases (for a particular doctor) in order to determine the factors involved in posterior leveling; these factors may then be used to evaluate a proposed leveling, e.g., using either a Naïve Bayes or a Tree-augmented Naïve Bayes model. By optimizing over the scorer, a recommendation can be generated. Finally, arch shape recommendations may recommend an arch shape for a given doctor and type of patient using a combination of elliptic Fourier descriptors and a collaborative filter based on matrix factorization (e.g., matrix factorization in 3 dimensions) in order to predict Elliptic Fourier Descriptor (EFD) components that are doctor and patient specific.

In some embodiments, described herein are methods for providing a leveling recommendation to a doctor for a patient's teeth, the method comprising: inputting into a computing system an initial anterior leveling dataset of the patient's anterior teeth; inputting into the computing system an incisor preference ($b_{pref}$) received from the doctor regarding a leveling position of lateral incisors; obtaining with the computing system an average anterior leveling ($\mu$) dataset derived from a plurality of patients; determining a final leveling dataset based on the initial anterior leveling dataset, the incisor preference received from the doctor and the average anterior leveling dataset; and displaying, to the doctor, a final leveling recommendation from the final leveling dataset.

These methods may also include determining leveling (e.g., a leveling dataset) including the posterior teeth as well, although in some variations, the posterior teeth may be excluded. Any of these methods may also include generating an orthodontic device from the final leveling dataset. For example, a method of providing a leveling recommendation may also include determining a posterior leveling dataset based on the patient's posterior teeth, and determining the dataset may comprise determining the final leveling data set based on the initial anterior leveling dataset, the incisor preference received from the doctor, the average anterior leveling dataset, and the posterior leveling dataset.

In any of the methods described herein, the final leveling recommendation (e.g., anterior, posterior, arch shape) may be displayed on the computing device, may be displayed as an output (visual, digital, printout), or may be displayed as a model (virtual, 3D fabricated, etc.) of the teeth and/or a dental appliance to be used on the teeth.

Determining the final leveling dataset may be based on at least one latent factor, wherein the at least one latent factor comprises one or more of: a country bias, a gender bias, a patient-type bias, and a doctor/gender bias. In particular, the latent factor may be a doctor/gender bias (e.g., $p_{dg}$).

The incisor preference ($b_{pref}$) may be received from the doctor regarding the leveling position of lateral incisors with respect to a leveling position of central incisors. This $b_{pref}$ may be a preference by the doctor that the lateral incisors be raised with respect to the central incisors, and/or a preference by the doctor that the lateral incisors be level with the central incisors, and/or a preference by the doctor that the lateral incisors and central incisors be leveled based gingival margins of the patient.

Determining a final leveling dataset may include or involve applying matrix factorization to matrices containing the initial anterior leveling dataset, the incisor preference ($b_{pref}$), and the average anterior leveling dataset ($\mu$).

The final leveling dataset may comprise a matrix containing a set of possible leveling recommendations and a score for each leveling recommendation. Any of these methods may include selecting the final leveling recommendation from the final leveling dataset. The selected final leveling recommendation may comprise a highest score from the set of possible leveling recommendations. The final leveling recommendation may be added to the average anterior leveling dataset.

As another example of a method for providing a leveling recommendation, described herein are methods for providing an anterior leveling recommendation to a doctor for a patient's teeth. The method may include: inputting into a computing system an initial anterior leveling dataset of the patient's anterior teeth; inputting into the computing system an incisor preference ($b_{pref}$) received from the doctor regarding a leveling position of lateral incisors; obtaining with the computing system an average anterior leveling (u) dataset derived from a plurality of patients; determining a final anterior leveling dataset based on the initial anterior leveling dataset, the incisor preference received from the doctor and the average anterior leveling dataset; and displaying, to the doctor, a final anterior leveling recommendation from the final leveling dataset.

A method for providing an arch shape recommendation to a doctor for a patient's dental arch may include: inputting into a computing system an initial arch shape dataset of the patient's dental arch; grouping the patient into a patient class based on the initial arch shape dataset; obtaining with the computing system an average arch shape dataset for the patient class; determining, with the computing system, a patient bias based on an average residual of arch shape recommendations for the patient class; determining, with the computing system, a doctor bias based on average residual of arch shape recommendations for the patient class made by the doctor; determining a final arch shape dataset based on the initial arch shape dataset, the patient bias, and the doctor bias; and displaying, to the doctor, a final arch shape recommendation from the final arch shape dataset. The methods for providing an arch shape recommendation may be part of a general method for providing a leveling recommendation to a doctor for a patient's teeth.

Determining the final arch shape may comprise applying matrix factorization to matrices containing the initial arch shape dataset, the patient bias, the doctor bias, and the average arch shape dataset. The final arch shape dataset may comprise a matrix containing a set of possible arch shape recommendations and a score for each arch shape recommendation.

Also described herein are methods for providing a leveling recommendation to a doctor for a patient's posterior teeth. For example, a method of providing a leveling recommendation to a doctor for a patient's posterior teeth may include: inputting into a computing system an initial posterior leveling dataset of the patient's posterior teeth; obtaining with the computing system an average posterior leveling dataset from a plurality of patients; determining a final posterior leveling dataset based on the initial posterior leveling dataset, the average posterior leveling dataset, and at least one factor from the initial posterior leveling dataset; and selecting a final posterior leveling recommendation from the final posterior leveling dataset. The methods for providing a leveling recommendation to a doctor for a patient's posterior teeth may be part of a general method for providing a leveling recommendation to a doctor for a patient's teeth. The at least one factor may comprise a leveling difference between corresponding teeth on a lower jaw and an upper jaw of the patient, and/or a leveling difference between corresponding teeth on a left and right side of a jaw of the patient, and/or an absolute leveling of at least one tooth. Determining may comprise using classifier theory to determine a probability distribution representing whether a given posterior leveling recommendation will be accepted by the doctor.

The selected final posterior leveling recommendation may comprise the highest probability from probability distribution. The final anterior leveling recommendation may be added to the average posterior leveling dataset.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1E illustrates an exemplary flowchart of a method for providing a leveling recommendation to a doctor for a patient's teeth as described herein.

DETAILED DESCRIPTION

The present disclosure is related to systems, methods, computing device readable media, and devices for creating an orthodontic aligner.

The planning and fabrication of such dental appliances as an example elastic polymeric positioning appliance is described in detail in U.S. Pat. No. 5,975,893, and in published PCT application WO 98/58596 which designates the United States, and which is herein incorporated by reference for all purposes. Systems of dental appliances employing technology described in U.S. Pat. No. 5,975,893, are commercially available from Align Technology, Inc., Santa Clara, Calif., under the tradename, Invisalign System. Align Technology, Inc.

Throughout the body of the Detailed Description, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances."

Factors involved in the leveling of teeth include symmetry, doctor preferences, preferences regarding gender, the country in which the patient is being treated, and other issues related to the aesthetics of the mouth and arch shape.

In general, described herein are methods for providing a leveling recommendation to a doctor for a patient's teeth. These leveling methods may be used for providing one or more of: anterior leveling recommendation, posterior leveling recommendations, and arch shape recommendations.

Figure 1A:
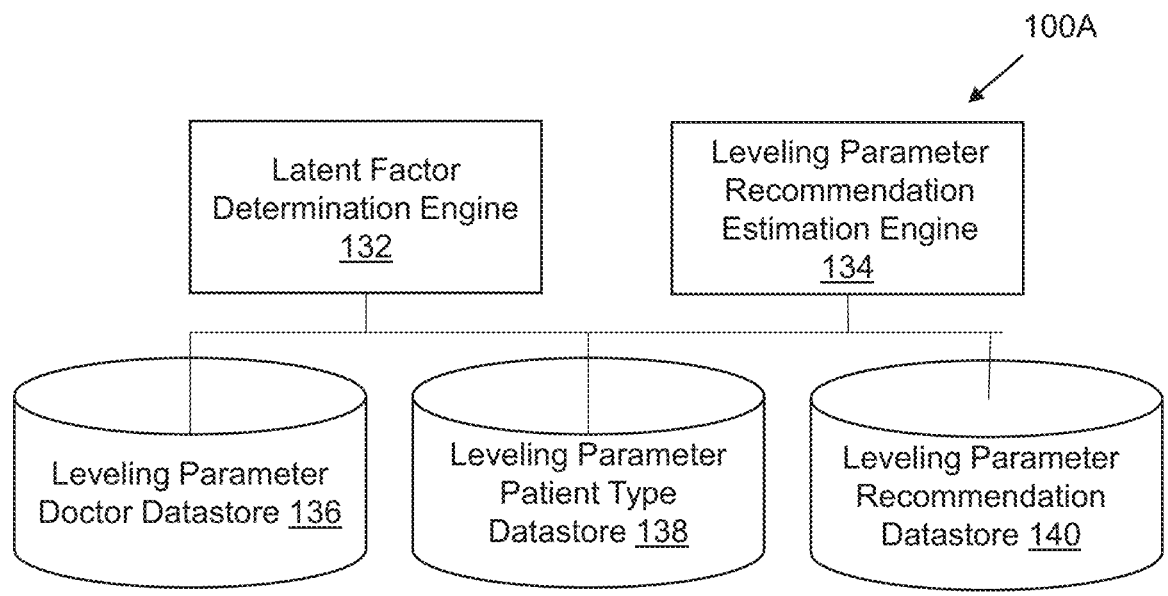
FIG. 1A shows an example of a system for estimating leveling recommendations using application of historical leveling parameters associated with doctors and application of historical leveling parameters associated with patient types.

FIG. 1A shows an example of a system 100A for estimating leveling recommendations using application of historical leveling parameters associated with doctors and application of historical leveling parameters associated with patient types. The system 100A may include engines and/or datastores. A computer system can be implemented as an engine, as part of an engine or through multiple engines. As used in this paper, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the FIGS. in this paper.

The engines described in this paper, or the engines through which the systems and devices described in this paper can be implemented, can be cloud-based engines. As used in this paper, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used in this paper, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described in this paper.

Datastores can include data structures. As used in this paper, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described in this paper, can be cloud-based datastores. A cloud-based datastore is a datastore that is compatible with cloud-based computing systems and engines.

In the example of FIG. 1A, the system 100A includes a latent factor determination engine 132, a leveling parameter recommendation engine 134, a leveling parameter doctor datastore 136, a leveling parameter patient type datastore 138, and a leveling parameter recommendation datastore 140. One or more of the modules of the system 100A may be coupled to one another or to modules not explicitly shown.

The latent factor determination engine 132 may be configured to estimate latent leveling factors using historical leveling parameters indexed by doctor and historical leveling parameters indexed by patient type. In some implementations, the latent factor determination engine 132 gathers first set of historic leveling parameters, each of the first set of the historic leveling parameters associated with a first set of doctors implementing a treatment plan. The latent factor determination engine 132 may further gather a second set of historic leveling parameters, where each of the second set of historic leveling parameters is associated with a first set of patient types of patients who have undergone the treatment plan.

The latent factor determination engine 132 may further be configured to derive from the first set of historical leveling data and the second set of historical leveling data a set of latent leveling factors that were used as the basis of prescribing the first and second set of historical data. One or more of the latent leveling factors may provide a latent statistical basis to associate the first set of the historic leveling parameters with the first set of doctors in the first dataset. One or more of the latent leveling factors may provide a basis to associate the second set of historical leveling parameters with the first set of patient types in the second dataset. The latent factor determination engine 132 may use automated agents to identify these latent leveling factors using techniques such as sparse-matrix factorization of the first dataset against the second dataset or vice versa.

The latent factor determination engine 132 may be configured to regularize the set of latent leveling factors. For instance, the latent factor determination engine 132 may be configured to determine whether one or more of the latent leveling factors exceeds a complexity threshold, and removing any latent leveling factors exceeding the complexity threshold. In some implementations, the latent factor determination engine 132 may be configured to identify whether one or more of the latent leveling factors correspond to bias by seeing if the latent leveling factors deviate from a known correlation between the first set of historic leveling parameters and the second set of historic leveling parameters. Examples of regularization and bias determination techniques are described in great detail herein.

The leveling parameter recommendation estimation engine 134 may be configured to use the latent leveling factors to derive a leveling recommendation for one or more combinations of doctors from the first set of doctors and patient types from one of the first set of patient types. Advantageously, the leveling recommendation may have a high likelihood of being applicable to future populations of doctors and/or patient types. Advantageously, the leveling recommendation may be based on latent leveling factors which were previously unknown and/or unknowable. In various implementations, the leveling parameter recommendation estimation engine 134 may be configured to store leveling recommendations for various combinations of doctors and patient types in the leveling parameter recommendation datastore 140.

The leveling parameter doctor datastore 136 may be configured to store historic leveling parameters provided by doctors at some time. The leveling parameter doctor datastore 136 may include a datastore that indexes leveling parameters prescribed in the past by doctor. In some implementations, the historical leveling parameters in the leveling parameter doctor datastore 136 implements a matrix of historic leveling recommendations by doctor. The leveling parameter patient type datastore 138 may be configured to store historic leveling parameters prescribed to different patient types over time. The leveling parameter patient type datastore 138 may include a datastore that indexes leveling recommendations by patient type. In various implementations, the leveling parameter patient type datastore 138 implements a matrix of historic leveling recommendations by patient type.

The leveling parameter recommendation datastore 140 may be configured to store latent leveling factors, such as those latent leveling factors identified and/or derived by the leveling parameter recommendation estimation engine 134.

Figure 1B:
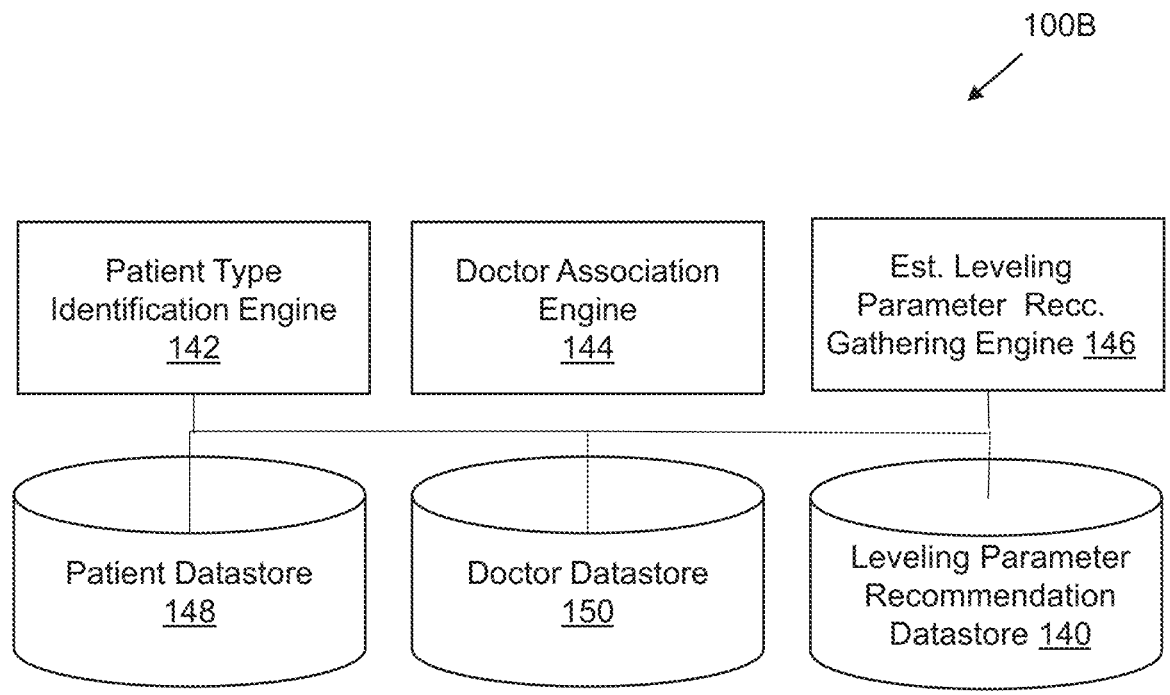
FIG. 1B shows an example of a system for generating leveling recommendations derived from latent leveling factors.

FIG. 1B shows an example of a system 100B for generating leveling recommendations derived from latent leveling factors. The system 100B may include a patient type identification engine 142, a doctor association engine 144, an estimated leveling parameter recommendation gathering engine 146, a patient datastore 148, a doctor datastore 150, and the leveling parameter recommendation datastore 140. One or more of the modules of the system 100B may be coupled to one another or to modules not explicitly shown.

The patient type identification engine 142 may be configured to gather patient data of one or more patients from the patient datastore 148. The patient type identification engine 142 may further be configured to identify patient types of patients whose information has been gathered. The doctor association engine 144 may be configured to gather from the doctor datastore 148 doctor identifiers of doctors implementing a treatment plan. The doctor association engine 144 may further be configured to associate patient data with a doctor identifier of a doctor implementing a treatment plan.

The estimated leveling parameter recommendation gathering engine 146 may be configured to identify one or more leveling recommendations for a doctor/patient type pair. In some implementations, the leveling recommendations are gathered from the leveling parameter recommendation datastore 140. As noted herein, the leveling parameters may provide latent statistical basis to associate a first set of the historic leveling parameters with a first set of doctors in a first dataset and further providing a basis to associate a second set of historical leveling parameters with a first set of patient types in a second dataset.

As also noted herein, leveling parameter recommendation datastore 140 may be configured to store latent leveling factors, such as those latent leveling factors identified and/or derived by the leveling parameter recommendation estimation engine 134 (see FIG. 1A).

The patent datastore 148 may include a datastore configured to store patient data of a patient. Such patient data may include identifiers of gender, heritage, and/or other background data of a patient as well as identifiers associated with jaw shape/size, arch shape/size, facial characteristics, and/or other physical characteristics. The patient data may form a basis to associate a patient with a patient type. The doctor datastore 150 may be configured to store doctor data of doctors. The doctor data may include identifiers of doctors as well as information about treatment plans that those doctors have implemented in the past.

Figure 1C:
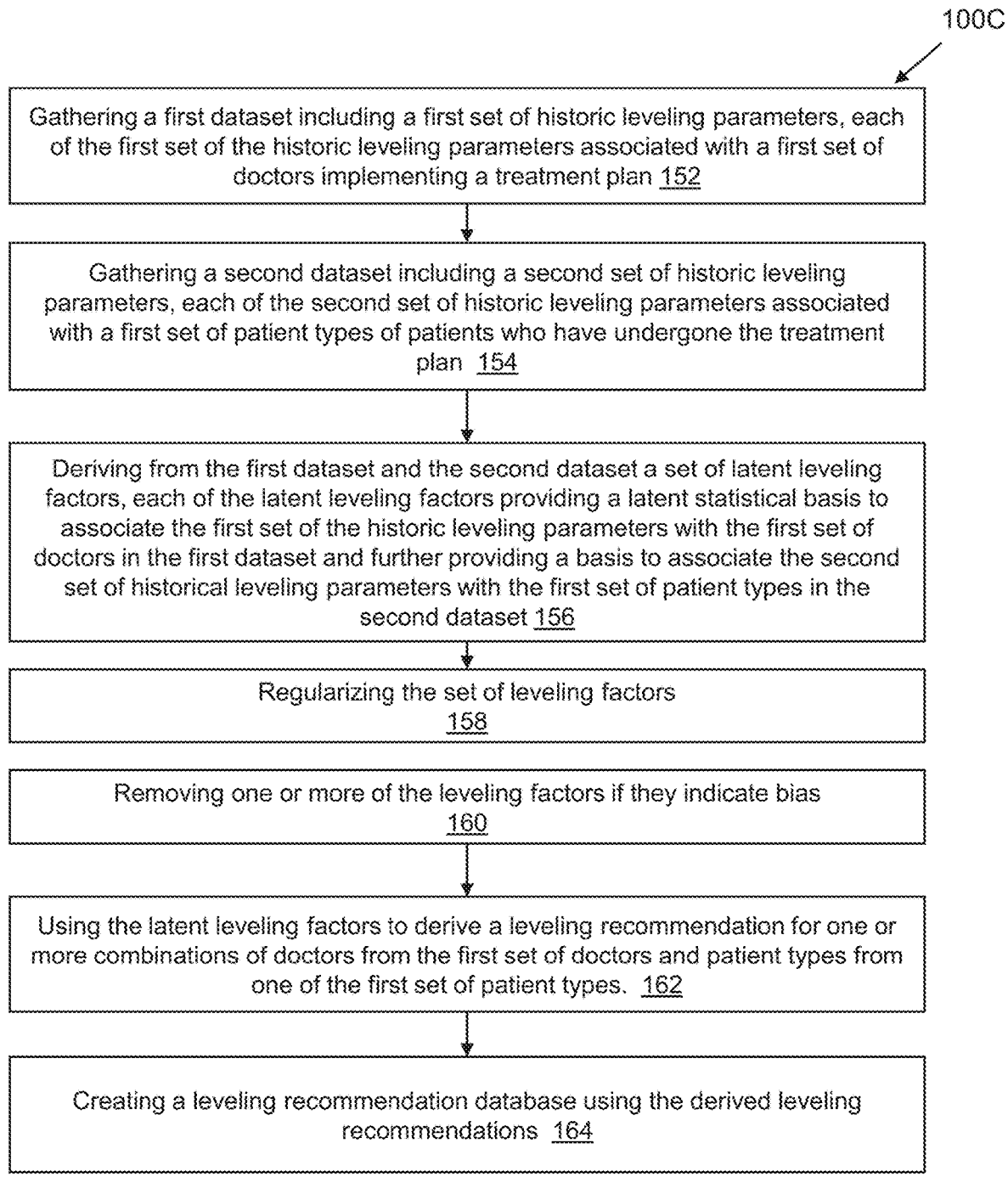
FIG. 1C shows an example of a method for estimating leveling recommendations using application of historical leveling parameters associated with doctors and application of historical leveling parameters associated with patient types.

FIG. 1C shows an example of a method 100C for estimating leveling recommendations using application of historical leveling parameters associated with doctors and application of historical leveling parameters associated with patient types. The method 100C may be executed by one or more modules described herein, including but not limited to the modules of the system 100A shown in FIG. 1A. It is noted the method 100C may include a greater or fewer number of operations than those depicted. It is noted other structures may operate to perform the operations of the method 100C.

At an operation 152, a first dataset including a first set of historic leveling parameters may be gathered. In some implementations, one or more of the first set of the historic leveling parameters is associated with a first set of doctors implementing a treatment plan. In some implementations, the latent factor determination engine 132 may gather from the leveling parameter doctor datastore 136 a first set of historic leveling parameters.

At an operation 154, a second dataset including a second set of historic leveling parameters may be gathered. In various implementations, one or more of the second set of historic leveling parameters is associated with a first set of patient types of patients who have undergone the treatment plan. As noted herein, the latent factor determination engine 132 may gather from the leveling parameter patient type datastore 138 a second set of historic leveling parameters where those historic leveling parameters are associated with a first set of patient types of patients who have undergone a treatment plan.

At an operation 156, a set of latent leveling factors may be derived from the first dataset and the second dataset. In various implementations, one or more of the latent leveling factors provides a latent statistical basis to associate the first set of the historic leveling parameters with the first set of doctors in the first dataset. One or more of the latent leveling factors may also provide a basis to associate the second set of historical leveling parameters with the first set of patient types in the second dataset. As discussed further herein, the leveling parameter recommendation estimation engine 134 may operate to derive a set of latent leveling factors from the first dataset and the second dataset.

At an operation 158, the set of leveling factors may be regularized. At an operation 160, one or more of the latent leveling factors may be removed if they indicate bias. The leveling parameter recommendation estimation engine 134 may operate to implement operations 158 and/or 160.

At an operation 162, the latent leveling factors may be used to derive a leveling recommendation for one or more combinations of doctors from the first set of doctors and patient types from one of the first set of patient types. The leveling parameter recommendation estimation engine 134 may operate, as discussed further herein, to derive a leveling recommendation for one or more combinations of doctors from the first set of doctors and patient types from one of the first set of patient types.

At an operation 164, a leveling recommendation database may be created using the derived leveling recommendations. As noted herein, the leveling parameter recommendation estimation engine 134 may operate to store one or more derived leveling recommendations in the leveling parameter recommendation datastore 140.

Figure 1D:
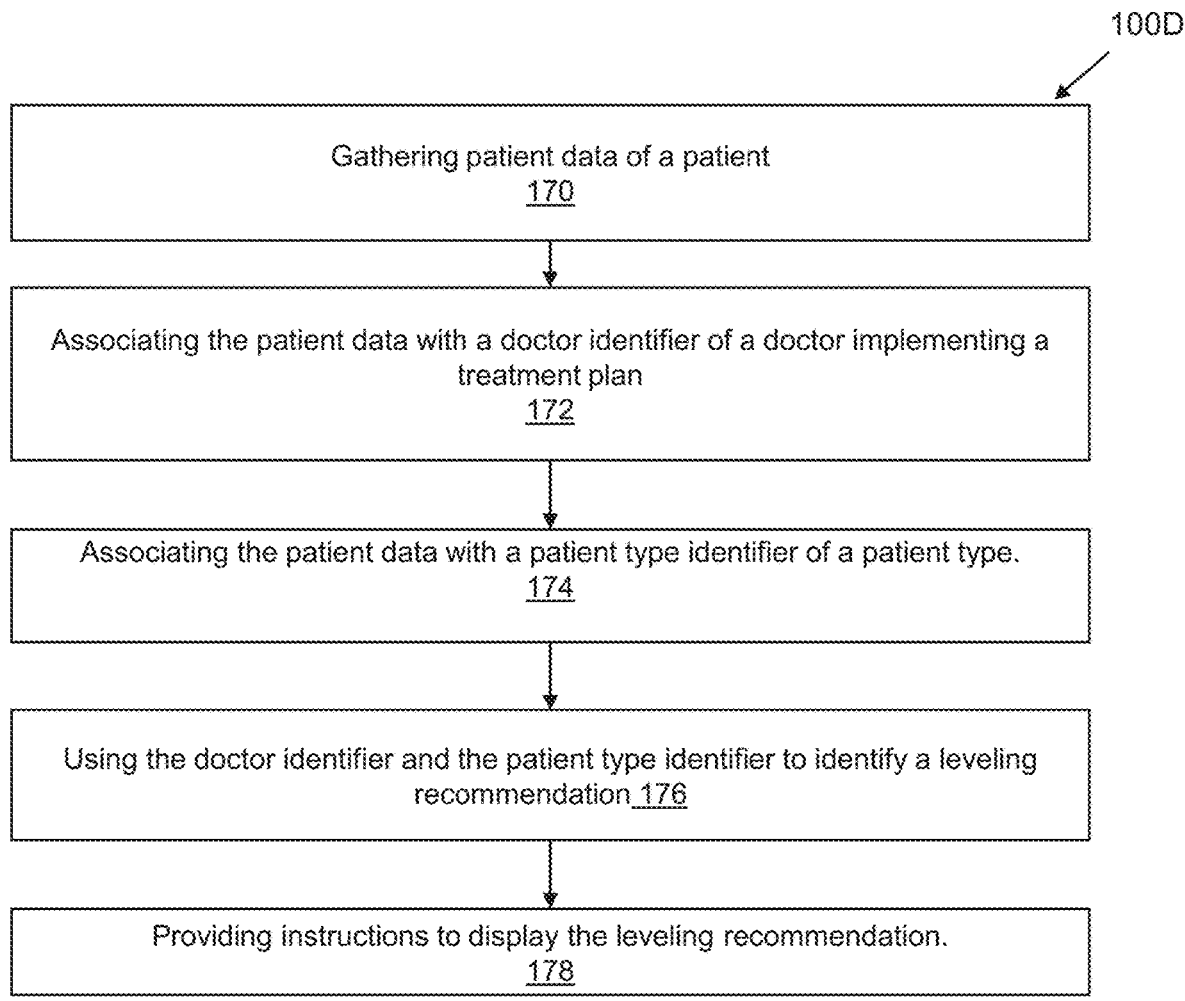
FIG. 1D shows an example of a method for generating leveling recommendations derived from latent leveling factors.

FIG. 1D shows an example of a method 100D for generating leveling recommendations derived from latent leveling factors. The method 100D may be executed by one or more modules described herein, including but not limited to the modules of the system 100B shown in FIG. 1B. It is noted the method 100D may include a greater or fewer number of operations than those depicted. It is noted other structures may operate to perform the operations of the method 100D.

At an operation 170, patient data of a patient is gathered. In some implementations, the patient type identification engine 142 may gather patient data from the patent datastore 148. The patient data may have been manually inputted, may have been crawled through one or more automated agents, or gathered from a larger universe of patient data using various data gathering techniques.

At an operation 172, the patient data is associated with a doctor identifier of a doctor implementing a treatment plan. The doctor association engine 144 may gather from the doctor datastore 148 a doctor identifier of a doctor implementing a treatment plan. At an operation 174, the patient data may be associated with a patient type identifier of a patient type. In some implementations, the patient type identification engine 142 may operate to associate the patient data with a patient type identifier of a patient type. The association may be due to, e.g., gender, heritage, and/or other background data of a patient as well as identifiers associated with jaw shape/size, arch shape/size, facial characteristics, and/or other physical characteristics.

At an operation 176, the doctor identifier and the patient type identifier may be used to identify a leveling recommendation. In some implementations, the leveling recommendation is derived from one or more latent leveling factors. As noted herein, in some implementations, the leveling factors provide a latent statistical basis to associate a first set of the historic leveling parameters with a first set of doctors in a first dataset. The leveling factors may further provide a basis to associate a second set of historical leveling parameters with a first set of patient types in a second dataset.

At an operation 178, instructions to display the leveling recommendation may be provided. In various implementations, the estimated leveling parameter recommendation gathering engine 146 may be configured to translate the leveling recommendation to a representation to be used in orthodontic treatment plans. As an example, in some implementations, the estimated leveling parameter recommendation gathering engine 146 may provide instructions to identify one or more 32-vector representations of leveling recommendations. As another example, the estimated leveling parameter recommendation gathering engine 146 may provide instructions to fabricate shell aligners, such as those used for an incremental orthodontic treatment plan, to implement the leveling recommendation.

FIG. 1E schematically illustrates one variation of a method for providing a leveling recommendation as will be described in greater detail below. In FIG. 1E, the method illustrated may include inputting (e.g., into a computing system) an initial anterior leveling dataset of the patient's anterior teeth 101. The user (e.g., doctor, dentist, technician, etc.) may then input an incisor preference ($b_{pref}$) regarding a leveling position of lateral incisors 103. The Incisor preference may indicate position of lateral incisors relative to central incisors. An average anterior leveling ($\mu$) dataset may then be derived from a plurality of patients 105, including datasets in a library or database of patient information. Based on this information, the method may then determine a final leveling dataset based on the initial anterior leveling dataset, the incisor preference received from the doctor and the average anterior leveling dataset 107. Determining a final leveling dataset may include latent factor such as country bias, gender bias, doctor/gender bias, etc.). As will be described in greater detail below, any of these methods may use matrix factorization to determine the final leveling dataset. The final leveling dataset may include possible leveling recommendations and a score for each leveling recommendation.

In some embodiments, the final leveling recommendation may be selected from the final leveling dataset 109 (e.g., the set having the highest score from the set of possible leveling recommendations). In some variations, the final leveling recommendation is added to the average anterior leveling dataset 111.

In any of these methods, a posterior leveling dataset may be determined based on the patient's posterior teeth (e.g., determining the dataset by determining the final leveling data set based on the initial anterior leveling dataset, the incisor preference received from the doctor, the average anterior leveling dataset, and the posterior leveling dataset) 113.

Once determined, the final leveling recommendation may be displayed (e.g., to the doctor), from the final leveling dataset 115.

Anterior Leveling Recommendation System using Sparse-matrix factorization

As mentioned above, matrix-factorization via a sparse version of singular value decomposition (SVD) can be deployed in a tooth-leveling recommendation system for anterior positioning of a patient's teeth and for determining arch shape.

When used with dense matrices, singular value decomposition of an m×n matrix M can be is represented as:

$$M = U\Sigma V^* \qquad (1)$$

where U is an m×m matrix, Σ is an m×n diagonal scaling matrix, and V* is an n×n matrix. In the context of a recommendation system, M can be considered to be a matrix where each row represents a user and each column represents an item. Cells of the matrix indicate a rating. The decomposition of M can be thought of as identifying a set of n latent factors (equivalent to the principal axes of a PCA) in the columns of V* and the mappings (UΣ) of the original rows onto the latent factors. The matrices are such that Σ is ordered from the most relevant factor to the least. The advantage of SVD is that the number of columns in U, the number of rows in V*, and the number of rows and columns in the scaling matrix Σ can be truncated to obtain a close approximation of M.

In a tooth-leveling recommendation system, this corresponds to finding the L most significant latent factors that represent the ratings of users for each item. This can be represented as factoring the rating matrix as:

$$M = PQ \qquad (2)$$

where M is the |users|×|items| matrix of ratings, P is a |users|×L matrix of users by latent factors, and Q is an L×|items| matrix of the latent factors for each item. M is a sparse matrix and the factorization cannot be performed by SVD. Instead, a parameter adjustment technique can be applied, such as Stochastic Gradient Descent (SGD), to attempt to learn the factorization from the sparse set of ratings.

To learn the factorization of the sparse rating matrix, the matrices P and Q can be initialized with some small values. Then, starting with the first latent factor l=1, iterating through each known rating for product i by user u, $r_{ui}$, and computing the current prediction of the rating:

$$\hat{r}_{ui} = \sum_{k=1}^{l} p_{uk} q_{ki} \qquad (3)$$

which is the sum of the user's preferences times the qualities of the item for all latent factors that have been completed so far are currently being worked on, l.

The error between the prediction and the actual rating is:

$$e_{ui} = r_{ui} - \hat{r}_{ui} \qquad (4)$$

Finding the best solution for P and Q is equivalent to minimizing the following over the entire set of ratings IC:

$$\min_{P,Q} \sum \left( r_{ui} - \sum_{k=1}^{l} p_{uk} q_{ki} \right)^2 \qquad (5)$$

which can be achieved using SGD by finding the derivative of the error with respect to P and Q:

$$\frac{\partial e_{ui}^2}{\partial p_{ul}} = 2e_{ui} \frac{\partial}{\partial p_{ul}} e_{ui} \qquad (6)$$

$$= 2e_{ui} \frac{\partial}{\partial p_{ul}} \left( r_{ui} - \sum_{k=1}^{l} p_{uk} q_{ki} \right) \qquad (7)$$

$$= -2e_{ui} q_{li} \qquad (8)$$

$$\frac{\partial e_{ui}^2}{\partial q_{li}} = 2e_{ui} \frac{\partial}{\partial q_{li}} e_{ui} \qquad (9)$$

$$= 2e_{ui} \frac{\partial}{\partial q_{li}} \left( r_{ui} - \sum_{k=1}^{l} p_{uk} q_{ki} \right) \qquad (10)$$

$$= -2e_{ui} p_{ul} \qquad (11)$$

and by moving P and Q in the opposite direction:

$$p_{ul} \leftarrow p_{ul} + \gamma e_{ui} q_{li} \qquad (12)$$

$$q_{li} \leftarrow q_{li} + \gamma e_{ui} p_{ul} \qquad (13)$$

where γ is a learning rate parameter and is typically set low at approximately 0.001.

By iterating over the entire set of ratings several times, the first latent factor, represented in the column vector pu1 and the row vector q1i, can be learned. The error can be minimized using the first latent factor, and the next latent factor l=2 can be learned through the same stochastic gradient descent algorithm. The process can then be repeated until all L factors are learned.

In practice, a latent factor model will have |users|×|items|×L parameters. It is common to have results with over one hundred million parameters. Thus, the model as stated is prone to over fitting. The solution to the over-fitting problem is regularization—penalizing complicated models in some way. The most common approach is to modify Equation 5 by including the $l_2$ norm of P and Q, indicated by ||•||.

$$\min_{P,Q} \sum_{(u,i) \in K} \left( r_{ui} - \sum_{k=1}^{l} p_{uk} q_{ki} \right)^2 + \lambda(\|P\|^2 + \|Q\|^2) \qquad (14)$$

since $$\frac{\partial}{\partial X} \|X\|^2 = \frac{\partial}{\partial X} Tr(XX^T) = 2X \qquad (15)$$

the update equations become:

$$p_{ul} \leftarrow p_{ul} + \gamma(e_{ui}q_{li} - \lambda p_{ul}) \quad (16)$$

$$q_{li} \leftarrow q_{li} + \gamma(e_{ui}p_{ul} - \lambda q_{li}) \quad (17)$$

To remove biases, Equation 3 can be replaced with:

$$\hat{r}_{ui} = \mu + b_u + b_i + \sum_{k=1}^{L} p_{uk}q_{ki} \quad (18)$$

where $\mu$ is the average of all item ratings, $b_i$ is the difference between the average rating of item i and $\mu$, and $b_u$ is the average over all $r_{ui} - b_i \cdot b_i$ can be thought of as the quality of the item with respect to all other items and $b_u$ is how easily user $\mu$ is satisfied. A basic predictor, using L=0, is then:

$$\hat{r}_{ui} = \mu + b_u + b_i \quad (19)$$

indicating that the prediction of user $\mu$'s rating of item i is the average of all ratings plus the difference in quality of item i as compared to the average plus the user's (lack of) pickiness.

As with the latent factors, the biases can then be regularized by finding the solution to:

$$\min_{b_i, b_u, P, Q} \sum \left( r_{ui} - \mu - b_u - b_i - \sum_{k=1}^{l} p_{uk}q_{ki} \right)^2 + \lambda(b_u^2 + b_i^2 + \|P\|^2 + \|Q\|^2) \quad (20)$$

This approach can first compute the average rating, $\mu$, then find the optimal, regularized set of $b_u$ and $b_i$ before finding the set of latent factors as described above using the update equations:

$$b_u \leftarrow b_u + \gamma(e_{ui} - \lambda b_u) \quad (21)$$

$$b_i \leftarrow b_i + \gamma(e_{ui} - \lambda b_i) \quad (22)$$

From the standpoint of recommendation systems for tooth-leveling that have been created to-date, there are a number of challenges with recommending a specific leveling:
1) an explicit set of training ratings does not exist, instead there is only an implicit rating of the final, accepted, leveling,
2) the implicit rating is no longer a scalar value, but is instead a vector of levelings, so that the matrix factorization approach as described above no longer applies directly, and
3) each patient only sees a single doctor, so there is only one recommendation per patient.

In the following disclosure, these issues are addressed and a new recommendation system is developed for tooth leveling that considers both the initial arch shape, initial tooth leveling, and learned doctor preferences.

Arch shapes are generally parameterized. The initial arch shape can be parameterized plus the initial leveling in RI and the final leveling in R32, where I is the number of basis vectors needed to represent the concatenation of the parameterized arch shape plus the parameterized initial tooth leveling.

Having parameterized the initial arch shape and leveling in RI and the final leveling in R32 it can be seen how recommendations might be implemented in a tooth leveling recommendation system.

In a typical rating system, a doctor considers a particular item and assigns it a rating, e.g., 1-5 stars. In our case, we only have implicit ratings, a given accepted leveling can be thought of as being rated highly, but we have no examples where a given doctor rates a leveling poorly, except for the initial levelings which are implicitly bad since they are to be corrected. A doctor provides a mapping from the initial arch shape and leveling to the final leveling:

$$f: \mathbb{R}^I \rightarrow \mathbb{R}^{32} \quad (23)$$

The doctor's mapping can be based on a number of biases plus latent factors. Rather than predicting a doctor's approval for a particular leveling (initial or final), the initial, parameterized patient data can be used to predict a final leveling directly.

Each bias can be represented as an leveling offset and the matrix vector product of a doctor's latent preferences (a vector of length L) can be computed with a matrix consisting of the patient's latent factors (of size 32×L).

The goal becomes the construction of a mapping on a per-doctor/per-patient basis. Unfortunately, a patient only sees a single doctor and has only one example of an initial arch, initial leveling, and final leveling for a given patient. The solution to this problem is to identify groups of patient arches by clustering the data using K-Means, agglomerative clustering, Birch, or some other appropriate algorithm for mapping $R^I$ to one of a set of patient types, P. This mapping considers how a given doctor will approach a given type of patient as compared to a different doctor examining a similar patient. Note, for this to be effective, the representation of the initial arch shape should be made in a scale and rotation invariant feature space such as is provided by normalized EFDs.

The leveling that was accepted for a given doctor, d, and patient type, p, can be termed $L_{pd}$. The leveling recommender will suggest an $\hat{L}_{pd}$ that will include the average final tooth leveling across the data set (mu or $\mu$), the leveling requested in the treatment form ($b_{pref}$ with values of Laterals0_5mmMoreGingivalThenCentrals, LateralsLevelWithCentrals, and GingivalMargins), a per-country bias ($b_c$), a per-gender bias ($b_g$), a per-patient type bias ($b_p$), and a per-doctor/per-gender bias ($b_{dg}$) plus a set of latent factors for each patient type, $A_p$, and the particular doctors preferences for those factors, $D_d$:

$$\hat{L}_{pd} = \mu + b_{pref} + b_c + b_g + b_p + b_{dg} + \sum_{l=1}^{L} d_d^l a_p^l \quad (24)$$

where $d_d^l$d is the 1-th latent factor for doctor d and $a_p^l$ is the 1-th latent vector for patient type p.

To compute the biases and the latent factors, initialize all $\hat{L}_{pd}$ can be initialized to =0. The error residual is then:

$$R_{pd} = L_{pd} - \hat{L}_{pd} \quad (25)$$

$$= L_{pd} - 0 \quad (26)$$

$$= L_{pd} \quad (27)$$

To find $\mu$, the following can be computed:

$$\mu = \frac{1}{|\mathcal{K}|} \sum_{j} R_j \quad (28)$$

and the residual can be updated:

$$R_j \leftarrow R_j - \mu : \forall j \in \mathcal{K} \quad (29)$$

To find the bias given the prescription form, a regularized $b_{pref}$ can be assumed as a Gaussian prior around 0 with N initial observations. The preferences bias is then:

$$b_{pref} = \frac{1}{|K^{pref}| + N} \sum R_j \quad (30)$$

where $K^{pref}$ is the subset of accepted leveling with a prescription form leveling preference, pref. Again, the residual is updated as:

$$R_j \leftarrow R_j - b_{pref}(j) : \forall j \in \mathcal{K} \quad (31)$$

where $b_{pref}$ (j) is the preference bias for the preference exhibited in case j.

Similarly, a regularized $b_c$ with a Gaussian prior around 0 with N initial observations can be found as:

$$b_c = \frac{1}{|K^c| + N} \sum R_j \quad (32)$$

where $K^c$ is the subset of accepted leveling from country, c. Again, the residual is updated as:

$$R_j \leftarrow R_j - b_c(j) : \forall j \in \mathcal{K} \quad (33)$$

where $b_c$ (j) is the country bias for the country in which case j occurred.

A regularized $b_g$ is found as:

$$b_g = \frac{1}{|K^g| + N} \sum R_j \quad (34)$$

where $K^g$ is the subset of accepted leveling for each gender, g. The residual is updated as:

$$R_j \leftarrow R_j - b_g(j) : \forall j \in \mathcal{K} \quad (35)$$

where $b_g$ (j) is the gender bias for case j.

The remaining biases can be found in a similar manner. Once the biases have been computed, the residual error remains which can be captured through a modified matrix factorization where the $D_d$ is the doctor's preferences for the latent factors represented in the 3-dimensional tensor $A_p$ which has dimensions L×P×32, where L is the number of latent factors, P is the number of patient types, and 32 represents the number of possible teeth in the leveling. In this scenario, the latent factors are per-patient class vectors of leveling deltas and a doctor's per-latent factor preference can be computed for this delta, so that the final prediction of the tooth leveling is as given in Equation 24, where $a_p^l$ represents the l-th latent factor for patient class p, and $d_d^l$ is doctor d's preference for the l-th latent factor.

There is no learning involved in computing $\mu$ or the various biases, however, both $a_p^l$ and $d_d^l$ can be learned such as stochastic gradient descent, where the update rules are as follows:

$$\frac{\partial}{\partial d_d} R_{pd}^T R_{pd} = -2R_{pd}^T a_p \quad (36)$$

$$\frac{\partial}{\partial a_p} R_{pd}^T R_{pd} = -2d_d R_{pd} \quad (37)$$

resulting in:

$$d_d^l \leftarrow d_d^l + \gamma R_{pd}^T a_p^l \quad (38)$$

$$a_p^l \leftarrow a_p^l + \gamma d_d^l R_{pd} \quad (39)$$

Having normalized the levelings in the dataset, the Anterior Leveling model and its individual subcomponents can be used to predict the doctor's accepted anterior leveling preferences based on the initial leveling, arch shape, and prescription form. As described in the previous sections, the initial arch shape is represented via the first principal components of a PCA of the Elliptic Fourier Descriptor representation of the arch points. The first 12 components of the normalized EFD can be used which captures essentially 100% of the explained variance in the data.

The input feature data can then be clustered into a plurality of patient types (e.g., 500 different patient types) using a batched K-means method. The model was then fit to the data, as described below.

Table 1 presents the results of running various portions of the anterior leveling model given in Equation 24. The metric used is the $\ell_2$ norm of the difference between the prediction and the doctor's anterior leveling.

TABLE 1

Various models for anterior tooth leveling prediction and their scores as compared to the doctor's accepted levelings.

| Model | Score |
|---|---|
| $L_{pd} = X_1$ | 788.41 |
| $L_{pd} = 0$ | 75.41 |
| $L_{pd} = \mu$ | 70.35 |
| $L_{pd} = \mu + b_{pref}$ | 6.84 |
| $L_{pd} = \mu + b_{pref} + b_g$ | 6.84 |
| $L_{pd} = \mu + b_{pref} + b_g + b_c$ | 6.83 |
| $L_{pd} = \mu + b_{pref} + b_g + b_c + b_p$ | 6.82 |
| $L_{pd} = \mu + b_{pref} + b_g + b_c + b_p + b_{dg}$ | 6.31 |
| $L_{pd} = \mu + b_{pref} + b_g + b_c + b_p + b_{dg} + \sum_{l=1}^{L} d_d^l a_p^l$ | 5.92 |
| $L_{pd} = \mu + b_g$ | 70.35 |
| $L_{pd} = \mu + b_c$ | 69.78 |
| $L_{pd} = \mu + b_p$ | 70.18 |
| $L_{pd} = \mu + b_{dg}$ | 35.45 |
| $L_{pd} = \mu + \sum_{l=1}^{L} d_d^l a_p^l$ | 16.89 |

As may be seen from the table able, when determining a final leveling dataset based on the patient's initial anterior leveling dataset using the methods described herein, it was surprisingly found that an average anterior leveling ($\mu$) dataset derived from a plurality of patients provided a dramatic increase in the predictive score (e.g., line three in table 1, above). More surprisingly, the addition of the doctor's incisor preference ($b_{pref}$) as received from the doctor regarding a leveling position of lateral incisors resulted in a much greater improvement in the predictive score (e.g., see line four in table 1, above). Other latent factors, including in particularly doctor/gender bias ($b_{dg}$) were also significant, but the use of at least $\mu$ and $b_{pref}$ provides a substantial increase in predictive strength.

Arch Shape Recommendation Using Sparse-Matrix Factorization

The same techniques as described above with respect to the anterior leveling recommendation system can be applied for an arch shape recommendation system.

From the standpoint of a recommendation system, there are a number of challenges with recommending an arch shape:

1) explicit set of training ratings does not exist, instead there is only an implicit rating of the final arch shape,
2) each patient only sees a single doctor, so there is only one recommendation per patient, and
3) the implicit rating is no longer a scalar value, but is instead a shape.

In the following disclosure, these issues are addressed and a new recommendation system is developed for arch shapes that considers both the initial arch shape and learned doctor preferences.

Arch shapes are generally parameterized. Both the initial and final (doctor-approved) arch positions can be parameterized for a patient using RI and RF respectively, where I and F are the number of basis vectors used to represent the initial and final arch shapes.

Having parameterized the initial and final arch shapes in RI and RF it can be seen how recommendations might be implemented.

A doctor can provide a function mapping the initial arch shape to the final:

$$f: \mathbb{R}^I \to \mathbb{R}^F \quad (40)$$

In matrix notation, if it is assumed that the initial arch shape is a column vector, x, and the final arch shape is a column vector, y, then:

$$y = Mx \quad (41)$$

Where M is a F×I transform matrix provided implicitly by the doctor.

The goal becomes constructing M on a per-doctor/per-patient basis, $M_{dp}$. Unfortunately, while this addresses the issue of a rating being a shape, it does not address the issue of a patient only seeing a single doctor and only having one example of an initial and final arch for a given patient.

The solution to this problem is to identify groups of patient arches by clustering the data using K-Means, agglomerative clustering, Birch, or some other appropriate algorithm for mapping $R^I$ to one of a set of patient types, P. This mapping considers how a given doctor will approach a given type of patient as compared to a different doctor examining a similar patient. Note, for this to be effective, the representation of the initial arch shape should be made in a scale and rotation invariant feature space such as is provided by EFDs.

While the issue of having multiple representations of arch types has been addressed, there remains a need to consider which factors are doctor-specific preferences and which are global factors for a given arch shape. To achieve this, $M_{dp}$ can be factored as $$M_{dp} = D_d A_p \quad (42)$$

Where $A_p$ is a F×I matrix that maps orthodontic practice for initial arch shape p to the final arch shape in $R^F$ and $D_d$ is a F×F matrix representing doctor d's preferences with respect to the final arch parameters. With this factorization, the relationship between the initial and suggested final arch shapes can be written as:

$$\hat{y} = D_d A_p x \quad (43)$$

As with any rating system, the system can be extended to remove biases to allow for multiple latent factors:

$$\hat{y}_{dp} = \left( \mu + b_d + b_p + \sum_{l=1}^{L} D_d^l A_p^l \right) x_p \quad (44)$$

Where $d_d^l$ and $a_p^l$ are l-th latent factor matrices.

Note that the system no longer fits into the SVD model of a single rating matrix being factored into a matrix of items with respect to their latent factors and a matrix of users and their preferences for latent factors. That said, the same least-squares approach used to estimate the factorization from a sparse set of ratings can still be used to determine the parameters of the arch recommendation system by utilizing SGD and a set of K of $(x_p, y_{dp})$ vectors. Given that:

$$e_{dp}^2 = e_{dp}^T e_{dp} = (y_{dp} - \hat{y}_{dp})^T (y_{dp} - \hat{y}_{dp}) \quad (45)$$

the goal is to minimize the error of the set by finding:

$$\min_{\mu, b_d, b_p, D_d, A_p} \sum e_{dp}^T e_{dp} \quad (46)$$

which can be found by taking the partial derivative of Equation 45 with respect to $\mu$, $b_d$, $b_p$, $D_d$, and $A_p$. When regularization is used to attempt to minimize the complexity of the parameters beyond the initial expectation that they be the identity matrix right padded with zero as necessary, I.

While the model above is mathematically very appealing, it has a large number of parameters which are not easy to learn (e.g., success is strongly dependent on the learning rate). In a second variant of the arch recommender, a clustering technique is again used to group the patients into a set of arch types, but instead of attempting to predict a transform matrix from the initial to accepted arch shape, the accepted arch shape is predicted directly based on latent factors. The model computes a bias, $\mu$ in $R^F$ by computing the average accepted arch shape in the first F dimensions of the PCA-computed space used above.

$$\mu = \frac{1}{|K|} \sum y_j - x_j \quad (47)$$

Since $\mu$ is the average difference between all accepted arch shapes and the initial arch shapes, $y_j = x_j + \mu$ is not expected to be an accurate approximation of the accepted arch shape, but it may normalize the data. To better approximate the accepted arch shape, biases can be added for both the patient-class and the doctor. The patient-class bias can be defined as $$b_p = \frac{1}{|K^p|} \sum y_j - x_j - \mu \quad (48)$$

where $K^p$ is the subset of the training arch shapes where the patient class is p. Note that this defines $b_p$ as the average residual of the accepted arches of class p and the average of all accepted arches, μ. Similarly, the doctor bias can be defined as:

$$b_d = \frac{1}{|K^d|} \sum y_j - x_j - \mu - b_p \qquad (49)$$

where $K^d$ is the subset of the training arch shapes where the doctor is d. This defines the doctor bias as being the average of the residual of the accepted arches with the average arch and the patient-class bias removed.

Now that the biases have been computed, a set of L latent factors can be utilized to describe the remaining residual. In this scenario, the latent factors are per-patient class vectors of arch shape deltas and we compute a doctor's per-latent factor preference for this delta, so that our final prediction of the arch shape is:

$$\hat{y}_{dp} = x_{dp} + \mu + b_p + b_d + \sum_{l=1}^{L} a_p^l d_d^l \qquad (50)$$

where $a_p^l$ represents the l-th latent factor for patient class p, and $d_d^l$ is doctor d's preference for the l-th latent factor.

In both variants described above, it is possible to weight the importance of different components of the arch shape when learning. One approach to this weighting is to consider the amount explained by each basis vector of the PCA. If v is a vector containing the normalized explained variance of the components of the PCA, then $$w = \frac{F}{\sum_{j=1}^{F} v_j} v \qquad (51)$$

where F is the number of components of the PCA that are being used.

Both variants described above were tested, but the second variant performed better and the results below are from that model. The process of learning was as follows:

1) Estimate initial arch shapes using the set of crown center x and y coordinates as a proxy for real information.
2) Compute the 20th degree elliptic Fourier descriptors for the initial arch shapes, storing the results in X
3) Compute the 20th degree elliptic Fourier descriptors for the accepted arch shapes, storing the results in Y
4) Compute the normalized version of the initial arch shapes as Xn
5) Cluster the normalized arch shapes, Xn into 1,000 patient types using mini-batch K-means, storing the classes in xclass
6) Fit a PCA of X, computing the fit on X and Y as Xp and Yp respectively
7) Truncate the number of columns of columns in $X_p$ and $Y_p$ to capture 99% of the variance in the PCA
8) Compute μ
9) Compute bp and bd
10) Learn the L=10 latent factors as described above The learning process substantially reduces the difference between the predicted arch shape and the accepted arch shape as compared to the initial arch.

Posterior Leveling Recommendation System Using Classifier Theory

Unlike anterior leveling in which aesthetic preferences are a primary concern, posterior leveling is driven primarily by clinical factors. The only strong per-doctor factor in posterior leveling is whether the doctor provided any posterior leveling at all. Rather than building a collaborative filtering model as was created for the anterior teeth as described above, the posterior leveling model of the present disclosure will be based primarily on the clinical factors as learned from the data.

The model will be heavily based on classifier theory where the two classes of interest are the "initial" leveling and the doctor's "accepted" leveling. In classifier theory, the Naïve Bayes Classifier relies upon Bayes' Theorem to predict whether a given set of observed variables correspond most closely to one class or another. Consider a classification problem with N classes, $C_1, \ldots, C_N$. Given a set of M observed variables, $\{X_1, \ldots, X_M\}$, the goal is to predict the probability of each class $C_n$ given X. From Bayes' Theorem, it is known that:

$$p(C_n | X) = \frac{p(X | C_n) p(C_n)}{p(X)} \qquad (52)$$

Since p(X) is a constant, it can be noted that:

$$p(C_n|X) \propto p(X|C_n) p(C_n) \qquad (53)$$

where p(Cn) is the prior probability of class n.

Considered in this way, an approach for comparing the probability that a given set of observed variables belongs to a given class as opposed to another class can be implemented by computing arg $\max_n p(C_n|X)$. The one remaining question is how to determine $p(C_n|X)$, particularly when X has a large number of variables. Unless the variables have been chosen carefully, they are almost certainly dependent upon each other. However, the Naïve Bayes assumption is that they are all independent, so:

$$p(X | C_n) = \prod_{m=1}^{M} p(X_m | C_n)$$

(54)

Figure 2A:
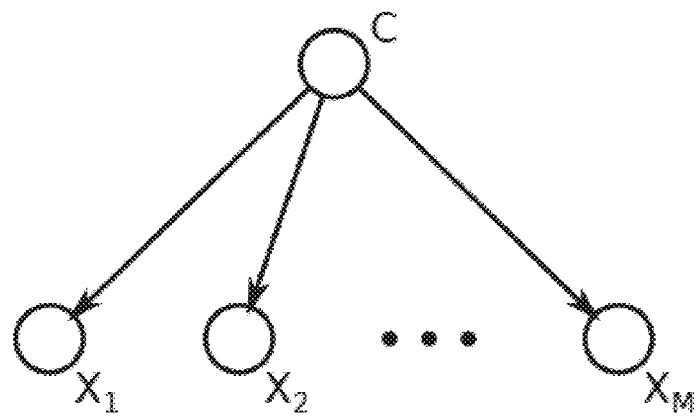
FIG. 2A is a graphical representation of the Naïve Bayes model.

Substituting Equation 54 into Equation 53 gives the overall probability of a particular class given a set of observed values, X, $$p(C_n | X) \propto p(C_n) \prod_{m=1}^{M} p(X_m | C_n) \qquad (55)$$

which can be represented as the graphical model in FIG. 2A.

To train the classifier, p(Cn|X) can be empirically computed for each variable, m, and each class, n. A number of approaches can be used for estimating the probability density function from a set of observed data, e.g., Gaussian Kernel Density Estimation. In this method $$p(x) = \frac{1}{N} \sum_{i=1}^{N} K(x - x_i) \qquad (56)$$

where K (•) is some kernel function, in this case Gaussian, xi is the set of observed values for x, and p(x) is the probability of some new point x given the observed values. The "width" of the Kernel function is generally estimated using either Scott's rule or Silverman's Rule.

One challenge of using Gaussian Kernel Density Estimation in practice is that each probability evaluation involves summing over a large number of Gaussian Kernels. In practice, it is more efficient to compute and store a piecewise interpolation function that approximates the Gaussian KDE.

For scoring potential levelings, it is difficult to consider a leveling and determine whether it comes from the class of "accepted" levelings or "rejected" levelings in part because there exists no sample of considered, but rejected levelings. Instead, consideration must be based on "initial" levelings which may have significant overlap with the class of accepted levelings. Due to this constraint, the probability that a given leveling would be accepted must be determined.

Figure 2B:
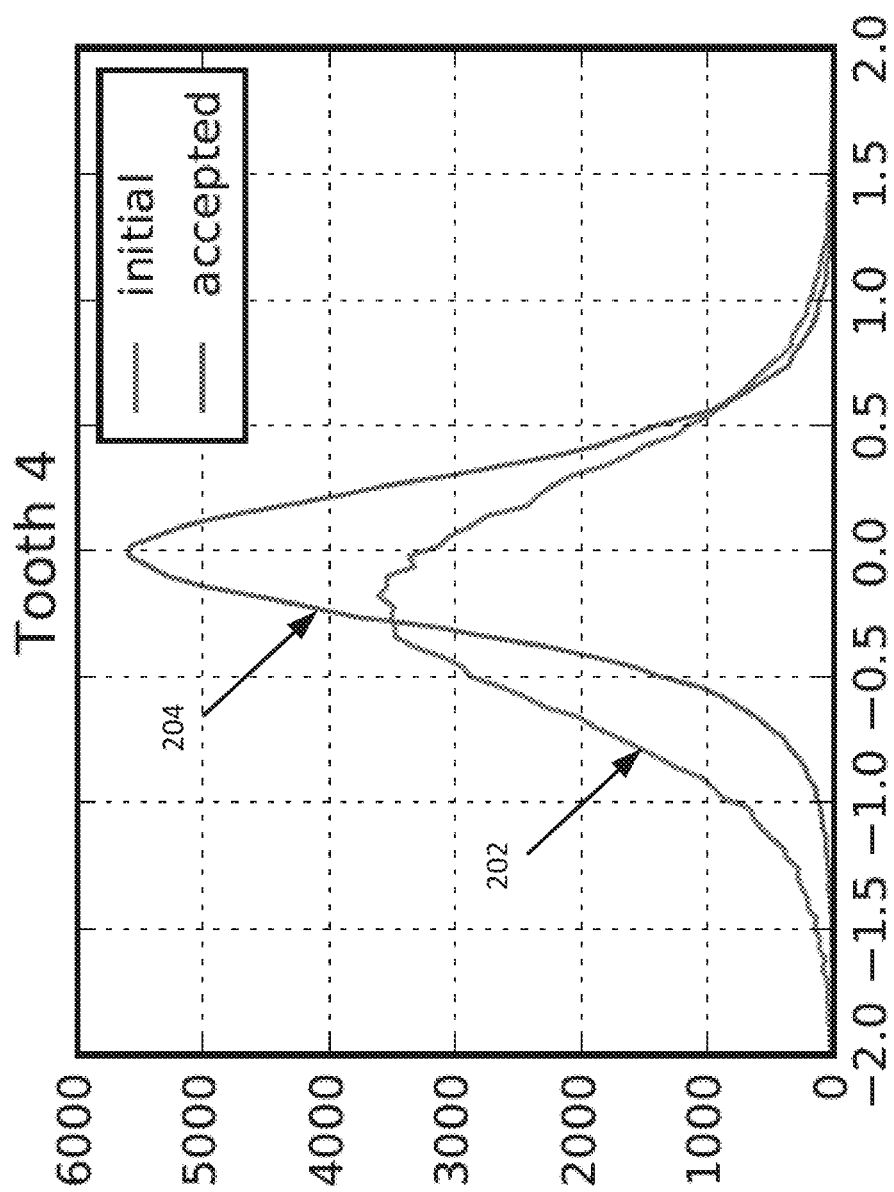
FIG. 2B shows an example of the initial distribution of levelings for tooth 4 and the accepted distribution of levelings.

One of the primary factors for consideration in the model is the absolute leveling of each tooth. FIG. 2B shows an example of the initial distribution of levelings for tooth 4 (line 202) and the accepted distribution of leveling (line 204). The Figure shows that, while the distributions overlap, the accepted position has a mean centered on 0, and has less variance around this value than does the initial position. The distributions of all 32 teeth follow this same pattern, though with some variation on the mean. If this histogram were converted to a probability density function, it would be more tightly peaked than a normal distribution with the same variance. This is different from the initial distribution which is very comparable to a normal distribution.

Figure 3:
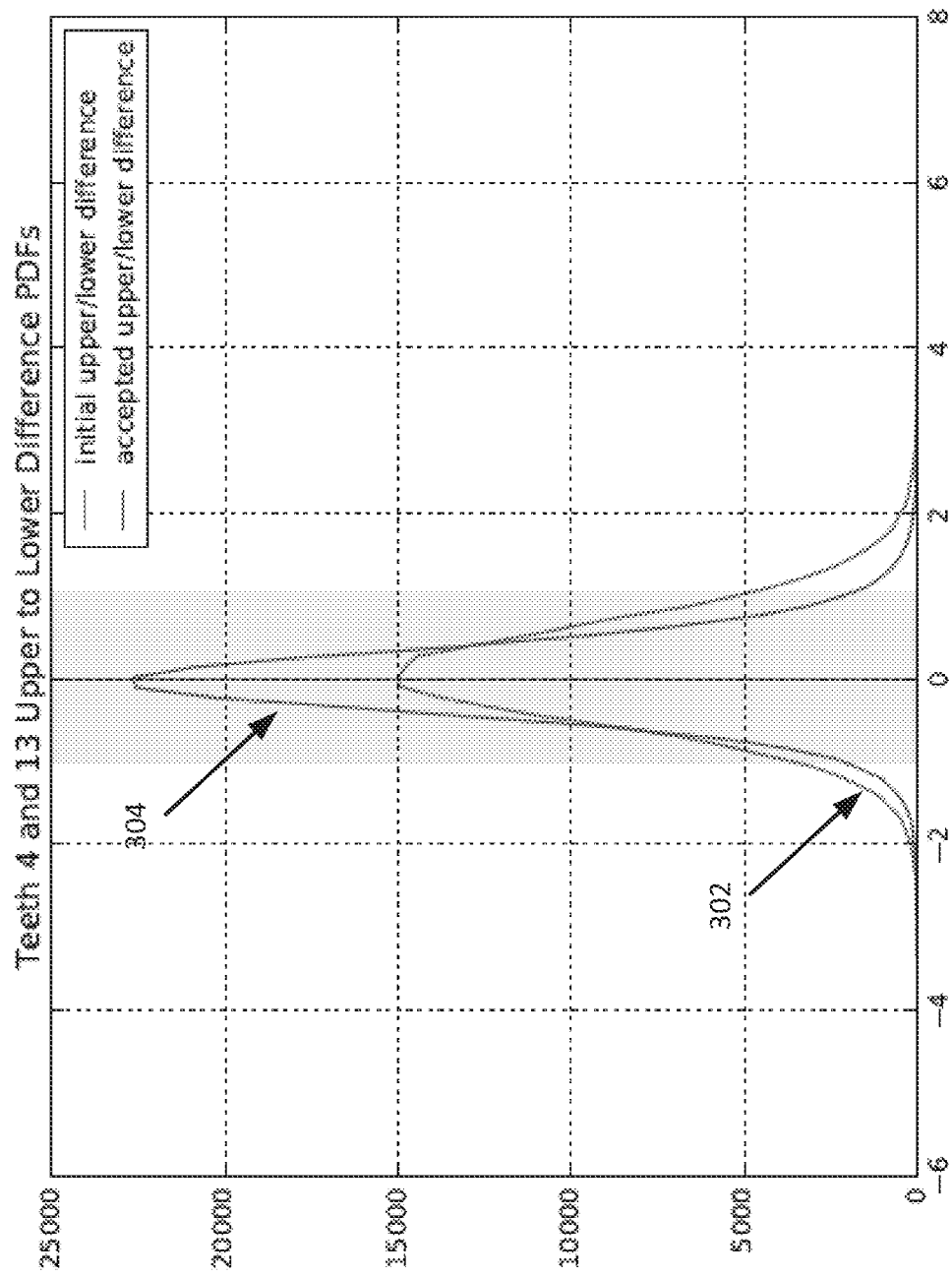
FIG. 3 is a sample distribution of upper to lower leveling for upper teeth 4 and 13 and their corresponding lower jaw teeth, 29 and 20, respectively.

Another factor in the quality of the leveling is the distance between the upper posterior teeth and the lower. In most cases, this centered around 0, but in some cases the mean of both the initial and the accepted difference is non-zero. For this feature, the difference in leveling is computed between the upper posterior teeth and their corresponding lower teeth. Additionally, facial symmetry can be taken advantage of to reduce the number of factors by considering each posterior tooth on the left side of the mouth with its corresponding tooth on the right side of the mouth. An example of this can be seen in FIG. 3 where both the initial (line 302) and accepted (line 304 distributions are centered around 0, but the accepted distribution is more strongly peaked, indicating some movement by doctors toward this position. Note, the shading indicates the 95% confidence interval for the accepted leveling.

Figure 4:
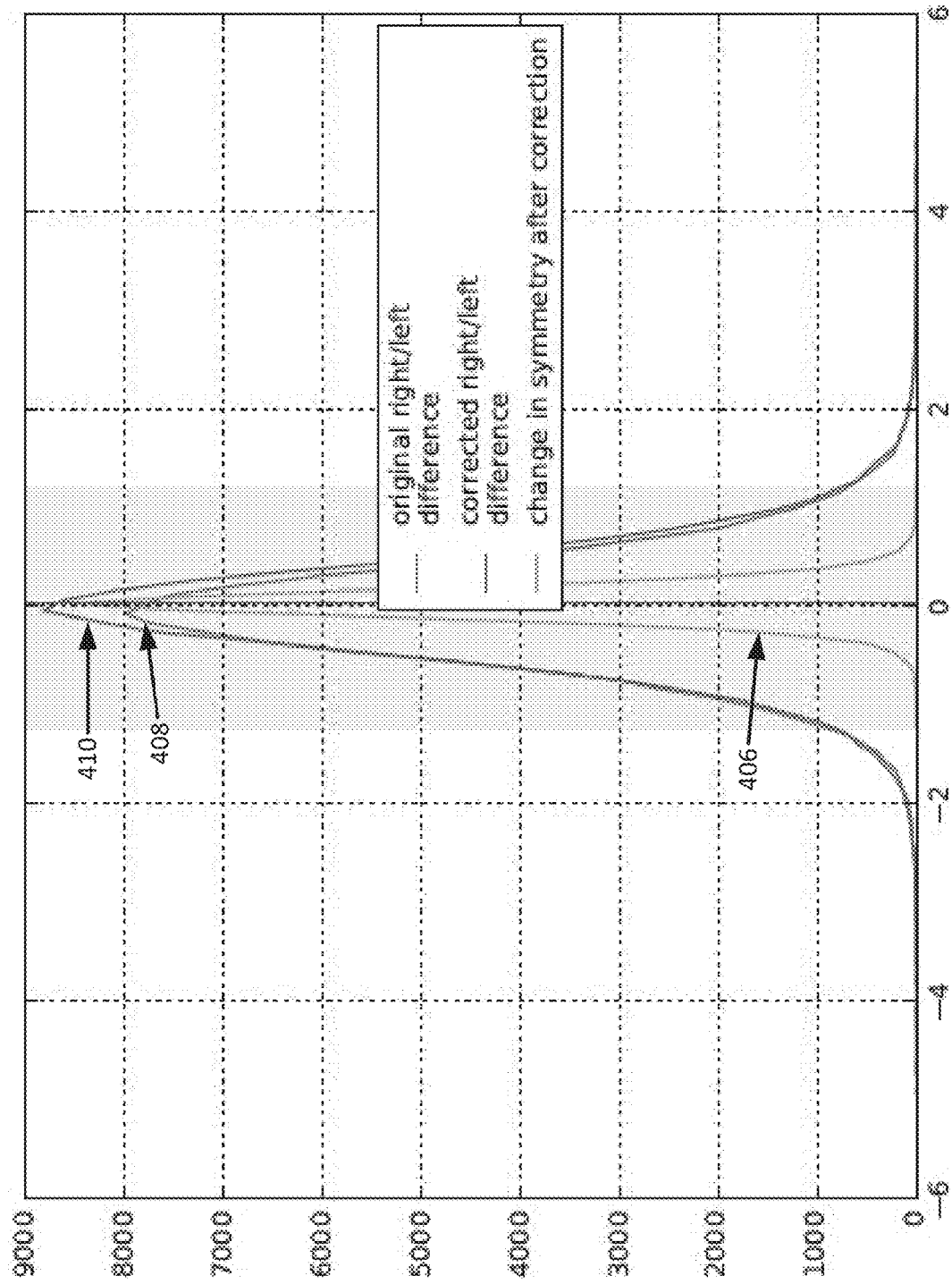
FIG. 4 shows facial symmetry sample distributions including an initial leveling symmetry distribution between teeth 5 and 12, a corrected symmetry distribution, and the change in symmetry after correction.

Symmetry is a very important factor when working with teeth. FIG. 4 considers the distribution around the symmetry of the accepted result. For any given patient, this considers the leveling of the teeth as compared to the leveling of the tooth on the opposite side of the mouth. In FIG. 4, this is seen in the change distribution line 406, which shows the change in symmetry after correction from the original distribution line 408 to the corrected distribution line 410.

In the previous section, left/right facial symmetry were considered. This feature considers the change in facial symmetry from the initial to the accepted distribution. In most cases, this is very tightly centered around 0, suggesting that the doctor is attempting to maintain the same facial symmetry differences as existed initially.

Figure 5:
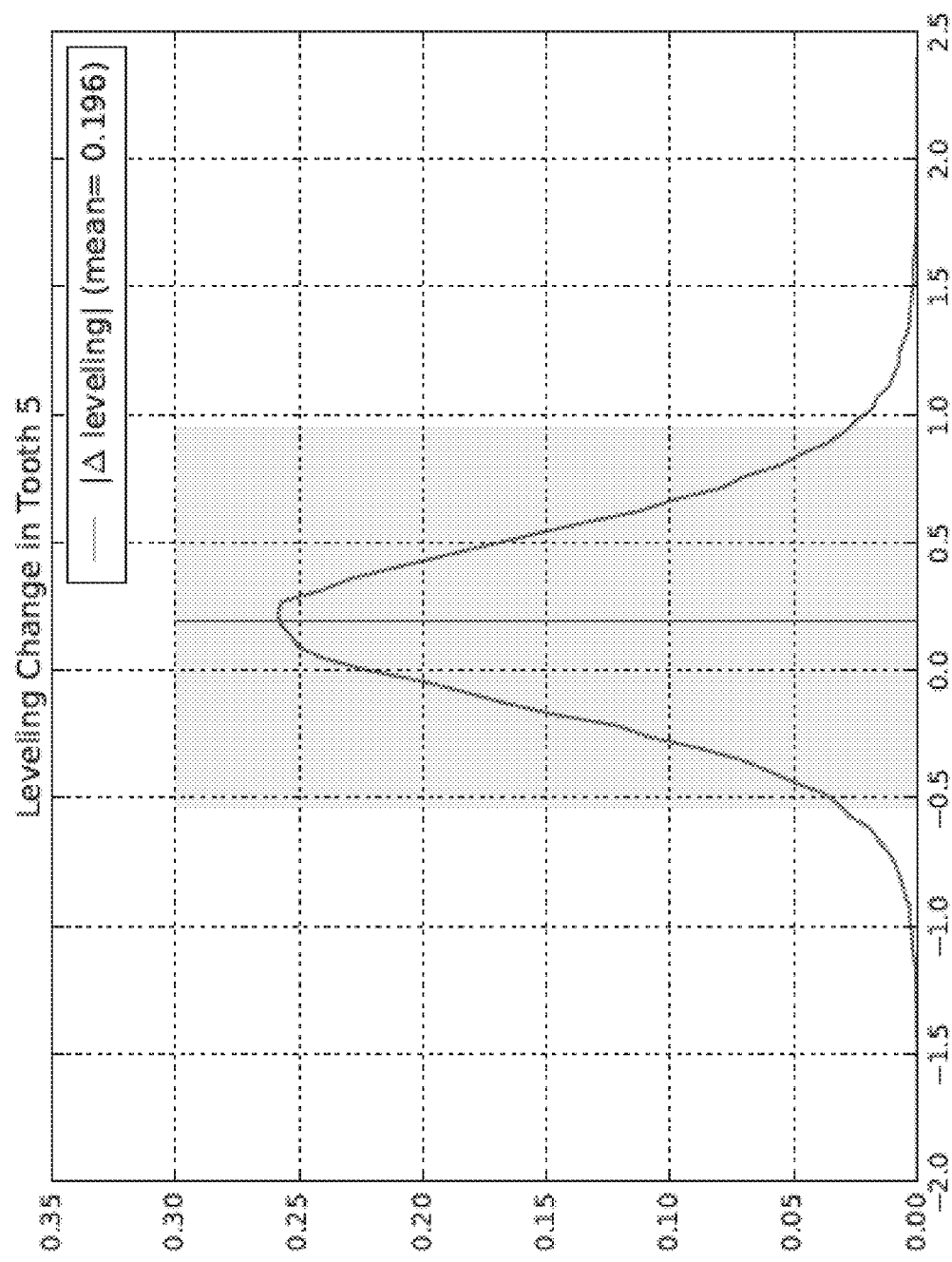
FIG. 5 shows a sample distribution over the change in leveling seen from initial to accepted in tooth 5.

Finally, the total difference between the accepted and initial levelings of each tooth can be considered. By considering how much change is typically seen per-case for each tooth, it can be determined whether a potential leveling recommendation is probable or even possible given the initial leveling. FIG. 5 shows a sample distribution over the change in leveling seen from initial to accepted in tooth 5.

In a normal Naïve Bayes classifier, the probabilities of each factor would be multiplied together, along with the class probability, to obtain an overall probability of seeing the factors given the class. Alternatively, for a more stable evaluation, the logarithm of the probabilities of each factor could be summed. Whichever class had the higher product (or sum) would be the class best represented by the data.

In this disclosure, the main concern is the raw probability of the data given the accepted class, so strict conformance to the Naïve Bayes classifier is not necessary. Instead, a normalized score can be used which allows the comparison of different patients even when they don't have the same set of teeth (and therefore don't have the same set of factors available for calculation). The score for a proposed leveling Y, given an initial leveling X can be computed as:

$$\text{score}(Y \mid X) = \frac{1}{|\mathcal{P}|} \sum_{i \in \mathcal{P}} \log p(Y_i) + \qquad (57)$$

$$\frac{1}{|\mathcal{J}|} \sum_{i,j \in \mathcal{J}} \log p(Y_i - Y_j) + \frac{1}{|S|} \sum_{i,j \in S} \log p(Y_i, Y_j \mid X_i, X_j) +$$

$$\frac{1}{|S|} \sum_{i,j \in S} \log p(Y_i - Y_j) + \frac{1}{|\mathcal{P}|} \sum_{i \in \mathcal{P}} \log p(Y_i - X_i)$$

where P is the set of posterior teeth, J is a set of tuples of the posterior teeth in the upper jaw and their corresponding lower tooth, and S is a set of tuples of the right teeth and their corresponding, symmetric tooth on the left.

Equation 57 can be used to score any arbitrary posterior leveling recommendation, including the recommendation of leaving the leveling at its initial position, score(X|X), which has the scoring advantage of not having changed its values and so having high values for log p(Yi,Yj|Xi, Xj) and log p(Yi–Xi). This requires any changes that are made in the leveling to improve the other factors in the model.

Another possible leveling recommendation is to use the most probable leveling across the model, Yi, =arg maxi p(Yi); vi. While this model will score high in terms of log p(Yi), log p(Yi–Yj), and log p(Yi–Xi), it may incur a significant change penalty from the remaining terms, possibly setting the score to –inf. Ideally, a posterior leveling can be identified that maximizes the score. There are a number of optimization techniques can be used, including line search Newton Conjugate Gradient method, BFGS, Nelder-Mead, the Powell method, and Sequential Least Squares Quadratic Programming (SLSQP). All of these methods, with the exception of the Powell Method, make use of either the exact or an estimate of the Jacobian, and the Newton Conjugate Gradient method requires the Hessian. Experimentally it has been found that the SLSQP method performs best in terms of both speed and optimization.

As described above, the Naïve Bayes Classifier model assumes independence between all of the variables $X_m$ in order to factor the conditional probability $p(X|C_n)$. In practice, this assumption of independence works reasonably well, often outperforming other state of the art classification methods. However, the independence assumption is often a limiting factor in the accuracy, and therefore performance, of the model. A more principled approach would consider the complete set of conditional probabilities between all of the various observed random variables in X. However, with even a relatively small number of random variables, this becomes intractable. The tree augmented Naïve Bayes algorithm attempts to address these problems by identifying the random variables with the greatest degree of mutual information and then models each variable as being dependent on, at most, one other random variable. The dependence relationships for the new model can then be represented by a tree.

The TAN model begins by constructing an M×M matrix, I where the pair-wise mutual information of the random variables will be stored:

$$I_{i,j} = \text{Mutual Information}(X_i, X_j) = I(X_i, X_j) \tag{58}$$

where:

$$I(X; Y) = \int_Y \int_X p(x, y) \log\left(\frac{p(x, y)}{p(x)p(y)}\right) dx dy, \tag{59}$$

which can be approximated as:

$$I(X; Y) = \sum_{y \in Y} \sum_{x \in X} p(x, y) \log\left(\frac{p(x, y)}{p(x)p(y)}\right), \tag{60}$$

when using the approximate Gaussian kernel density estimations.

I can then be used as the weights of a fully connected graph, G, which represents the degree of dependence between the variables. G can be converted into a tree, T, by finding the maximum-weighted spanning tree, using an algorithm such as Dijkstra's or Prim's, then selecting an arbitrary node to be the root node of the tree.

Figure 6:
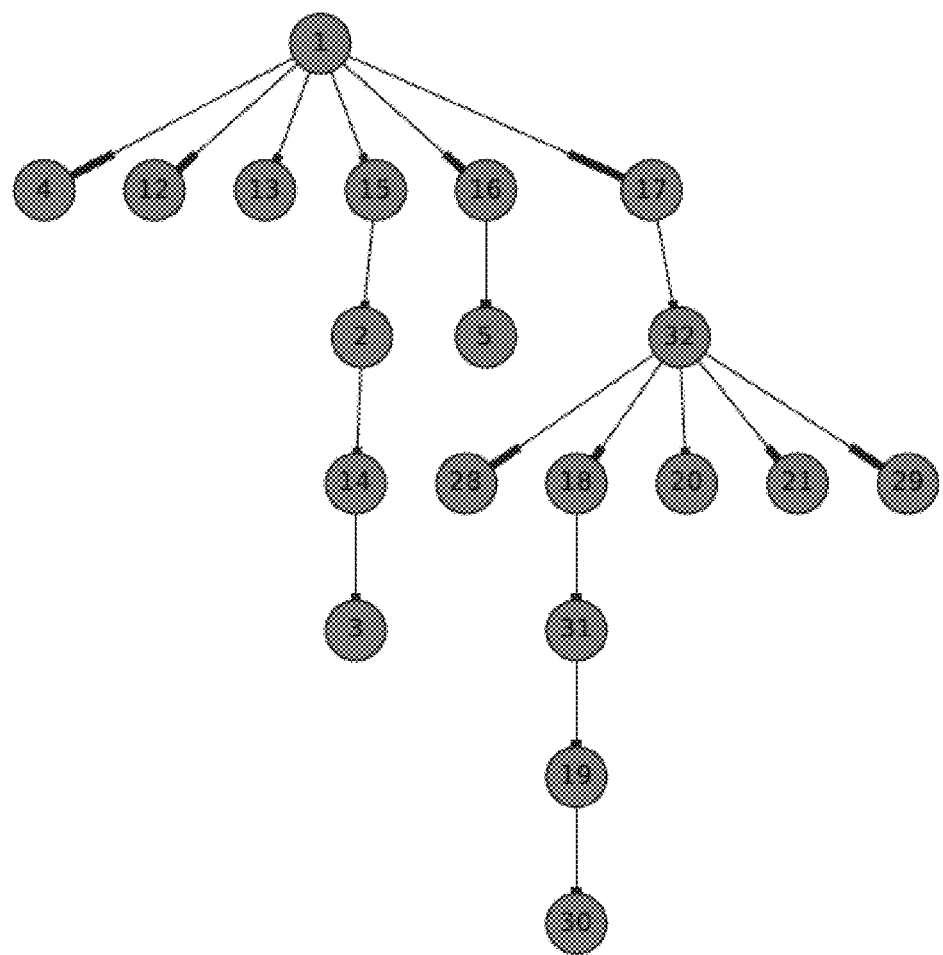
FIG. 6 shows a spanning tree that models dependence between variables using mutual information. The node labels indicate tooth number.

Once constructed, T can be used as a graphical model representing the dependency between variables. Consider the following example of a tree constructed from a subset of variables from the per-tooth change in leveling technique described above. With 20 posterior teeth, there are 20 factors in this model (M=20). The pairwise mutual information can be used to construct the tree shown in FIG. 6.

Since the data does not support the idea of doctor preferences, the posterior model was used to determine a best practice recommendation. For performance reasons, an approximation of the Gaussian KDE was used for probability density estimation. For each probability model of the form p(X|A), a 200-point piecewise linear interpolation function was used over the range of the function which resulted in a substantial performance improvement over computing the Gaussian KDE. To create "optimal" posterior levelings, the Sequential Least Squares Quadratic Programming optimizer built into Python's SciPy module was used with an initial solution of the initial teeth leveling.

As has been previously discussed, a doctor's decisions about posterior leveling appear to be based less on aesthetics and more on clinical factors. Overall, the model's score of the original levelings (which is of course not penalized by moving any teeth) indicated an average score of −1.30 which implies that the original levelings are relatively improbable as accepted final levelings. The doctor's accepted levelings had an average score of −0.87 which indicates a better fit with the model.

Using the Sequential Least Squares Quadratic Programming optimization, leveling were found with an average score of 0.45 which is a significant improvement in the fit with the model (recall that the scores are an average log of the probability of the features).

60% of the accepted levelings had a better score than the initial levelings and 89% of the optimal levelings were better than the accepted levelings. It is likely that more of the accepted levelings would have a better score except that the initial levelings received a bonus (of sorts) by not moving any of the teeth (high log p(Yi–Xi)).

To get a better sense of the strength of the Naive Bayes scorer, two scorers were trained, one using the initial data and one using the accepted data. To avoid having the initial scorer strongly penalize any movement, the features that considered the difference in position between the initial and accepted positions were removed. Once the two scorers were trained, a classification score was computed of the form:

$$\text{Score}_{total} = \text{Score}_{accept}(X, Y) - \text{Score}_{init}(X, Y). \tag{61}$$

This was then run against the initial and accepted positions to see if the accepted positions could be correctly identified from the model.

In a similar manner, the Tree Augmented Naïve Bayes model was also tested. In theory, this model which captures some of the dependencies, rather than assuming independence, should have better performance.

By separating the anterior and posterior leveling problems, the present disclosure has identified a pair of algorithms for making recommendations regarding tooth leveling. In general, these algorithms perform very well, capturing doctor's aesthetic preferences for anterior teeth and general clinical best practices for posterior teeth.

In considering the anterior teeth leveling model, a number of observations can be made. First, the model itself does not necessarily have enough information to capture all of the variance in teeth-types. For example, a patient with chipped teeth may have leveling needs that are different than a standard patient, even when the doctor's leveling preference is considered. Second, the simple model of predicting an anterior leveling based solely on the mean plus the doctor's indicated preference on the prescription form captures the almost all of the information regarding the doctor's accepted anterior leveling. Similarly, the latent model without knowledge of the doctor's preference captures a large fraction of the information with an error of 16.89. This suggests that the doctor's general preferences can be learned from the data alone and compares favorably to a model in which the mean is added to the doctor's stated generic preference for tooth leveling which has an error of 10.69.

In general, it is suggested to truncate the model to the mean plus the doctor's leveling preference as stated in the prescription form. Moreover, gender, country, and patient-type have little effect on the error of the model and while doctor preference per patient-type does have an effect, it is likely to be produced primarily by over fitting the parameters.

The posterior leveling model allows suggesting and scoring a variety of levelings.

The posterior leveling model currently relies on a Naïve Bayes assumption.

Figure 7:
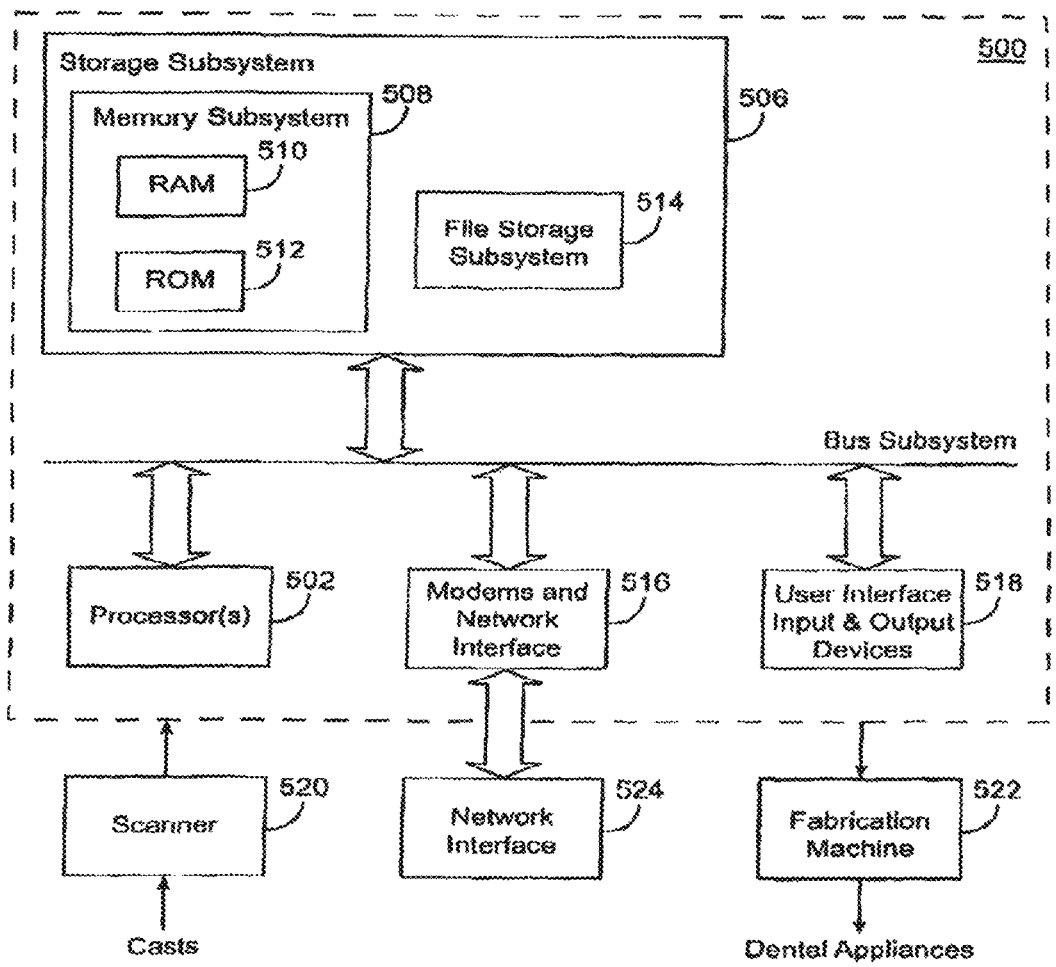
FIG. 7 is a simplified block diagram of a data processing system for designing and manufacturing an orthodontic aligner using leveling recommendations derived from latent leveling factors.

FIG. 7 is a simplified block diagram of a data processing system 500. Data processing system 500 typically includes at least one processor 502 which communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system).

File storage subsystem 514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524.

Fabrication machine 522 fabricates dental appliances based on intermediate and final data set information received from data processing system 500. In a distributed environment, fabrication machine 522 may be located at a remote location and receive data set information from data processing system 500 over network interface 524.

Figure 8:
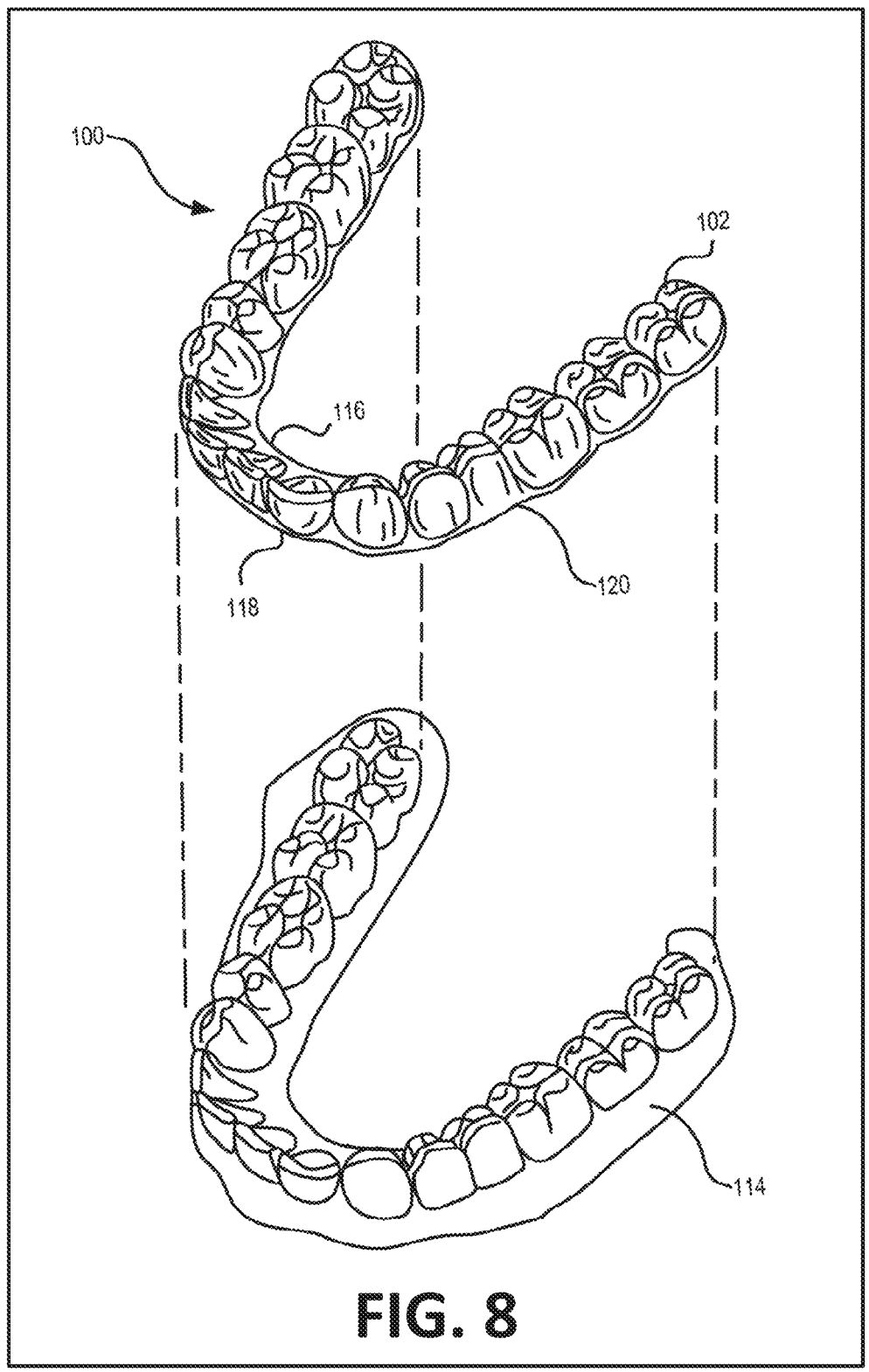
FIG. 8 shows an orthodontic aligner manufactured according to the algorithms described herein.

FIG. 8 shows the lower jaw 114 of a patient together with an orthodontic aligner 100, which can be designed according to the methods and techniques described above. The orthodontic aligner 100 is removable and replaceable over the teeth. In some embodiments, orthodontic aligner 100 is one of a plurality of incremental position adjustment appliances.

The orthodontic aligner 100 may comprise a polymeric concave trough 102 having an inner cavity 120, a proximal edge 116, and a distal edge 118. The inner cavity is shaped to receive and resiliently reposition teeth from one tooth arrangement to a successive tooth arrangement. In some embodiments, the polymeric concave trough 102 fits over all teeth present in the upper jaw (not depicted) or lower jaw 114.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method comprising:
  gathering an intraoral scan of dentition of a patient;
  obtaining a virtual model of the dentition using the intraoral scan;
  gathering patient data of the patient to receive orthodontic treatment in accordance with an orthodontic treatment plan;
  associating the patient data with a patient type identifier of a patient type related to the patient, the patient type representing a larger group of orthodontic treatment patients under which to group the patient;

using a doctor identifier and the patient type identifier to identify a leveling recommendation, wherein the leveling recommendation comprises one or more recommendations to intrude or extrude the dentition relative to gums of the patient, wherein the leveling recommendation is based on one or more latent leveling factors, wherein the one or more latent leveling factors provide a latent statistical basis to associate a first set of an historic leveling parameters with a first set of doctors in a first dataset and further provide a basis to associate a second set of the historic leveling parameters with a first set of patient types in a second dataset;

gathering the first dataset, the first dataset including the first set of the historic leveling parameters associated with the first set of doctors implementing a treatment plan;

gathering the second dataset, the second dataset including the second set of historic leveling parameters associated with the first set of patient types of patients who have undergone the treatment plan;

deriving from the first dataset and the second dataset the one or more latent leveling factors;

identifying whether one or more of the latent leveling factors correspond to bias by seeing if the one or more latent leveling factors deviate from a known correlation between the first set of historic leveling parameters and the second set of historic leveling parameters;

using the one or more latent leveling factors to derive a derived leveling recommendation for one or more combinations of doctors from the first set of doctors and patient types from one of the first set of patient types;

creating the leveling recommendation using the derived leveling recommendation;

providing instructions to display the leveling recommendation; and displaying the leveling recommendation on a three-dimensional (3D) virtual model of a jaw of the patient.

2. The method of claim 1, further comprising providing instructions to design one or more orthodontic aligners to implement the leveling recommendation as part of the orthodontic treatment plan.

3. The method of claim 1, wherein the patient type corresponds to one or more of a gender, a heritage, or other background of the patient.

4. The method of claim 1, wherein the patient type corresponds to one or more of a jaw shape/size, an arch shape/size, a facial characteristic, or physical characteristic of the patient.

5. The method of claim 1, wherein the leveling recommendation is displayed using a thirty-two (32) bit vector representation of a dentition of the patient.

6. The method of claim 1, wherein deriving the one or more latent leveling factors comprises performing sparse matrix factorization of the first dataset against the second set.

7. The method of claim 1, further comprising regularizing the set of the one or more latent leveling factors by determining whether one or more of the latent leveling factors exceeds a complexity threshold, and removing any latent leveling factors exceeding the complexity threshold.

8. The method of claim 1, further comprising displaying the leveling recommendation on a three-dimensional (3D) virtual model of a jaw of the patient.

9. The method of claim 1, further comprising providing instructions to design one or more orthodontic aligners to implement the leveling recommendation as part of the orthodontic treatment plan.

10. The method of claim 1, wherein the patient type corresponds to one or more of a gender, a heritage, or other background of the patient.

11. The method of claim 1, wherein the patient type corresponds to one or more of a jaw shape/size, an arch shape/size, a facial characteristic, or physical characteristic of the patient.

12. The method of claim 1, wherein the leveling recommendation is displayed using a thirty-two (32) bit vector representation of a dentition of the patient.

13. A system comprising:
one or more processors;
memory coupled to the one or more processors, the memory configured to store computer-program instructions, that, when executed by the one or more processors, implement a computer-implemented method, the computer-implemented method comprising:
gathering an intraoral scan of dentition of a patient;
obtaining a virtual model of the dentition using the intraoral scan;
gathering patient data of the patient to receive orthodontic treatment in accordance with an orthodontic treatment plan;
associating the patient data with a patient type identifier of a patient type related to the patient, the patient type representing a larger group of orthodontic treatment patients under which to group the patient;
using a doctor identifier and the patient type identifier to identify a leveling recommendation, wherein the leveling recommendation comprises one or more recommendations to intrude or extrude the dentition relative to gums of the patient, wherein the leveling recommendation is derived from one or more latent leveling factors, wherein the one or more latent leveling factors provide a latent statistical basis to associate a first set of an historic leveling parameters with a first set of doctors in a first dataset and further providing a basis to associate a second set of the historic leveling parameters with a first set of patient types in a second dataset;
gathering the first dataset, the first dataset including the first set of the historic leveling parameters associated with the first set of doctors implementing a treatment plan
gathering the second dataset, the second dataset including the second set of historic leveling parameters associated with the first set of patient types of patients who have undergone the treatment plan;
deriving from the first dataset and the second dataset the one or more latent leveling factors;
identifying whether one or more of the latent leveling factors correspond to bias by seeing if the one or more latent leveling factors deviate from a known correlation between the first set of historic leveling parameters and the second set of historic leveling parameters;
using the one or more latent leveling factors to derive a derived leveling recommendation for one or more combinations of doctors from the first set of doctors and patient types from one of the first set of patient types;
creating the leveling recommendation using the derived leveling recommendation;
identifying whether one or more of the latent leveling factors correspond to bias by seeing if the one or more latent leveling factors deviate from a known correlation between the first set of historic leveling parameters and the second set of historic leveling parameters; and
providing instructions to display the leveling recommendation.

* * * * *